United States Patent [19]

Kuwahara et al.

[11] Patent Number: 5,041,987
[45] Date of Patent: Aug. 20, 1991

[54] METHOD FOR PREDICTING AND CONTROLLING THE STRENGTH DEVELOPMENT OF CONCRETE AND APPARATUS THEREFOR

[75] Inventors: Takashi Kuwahara; Nobuyuki Yamazaki, both of Tokyo, Japan

[73] Assignee: Shimizu Construction Co., Ltd., Tokyo, Japan

[21] Appl. No.: 453,189

[22] Filed: Dec. 19, 1989

Related U.S. Application Data

[63] Continuation of Ser. No. 116,726, Nov. 4, 1987, abandoned.

[30] Foreign Application Priority Data

| Nov. 4, 1986 | [JP] | Japan | 61-262270 |
| Nov. 4, 1986 | [JP] | Japan | 61-262271 |
| Nov. 4, 1986 | [JP] | Japan | 61-262272 |
| Dec. 5, 1986 | [JP] | Japan | 61-289901 |

[51] Int. Cl.$^5$ .............................................. G01N 3/26
[52] U.S. Cl. .................................... 364/505; 364/550; 364/552; 340/665; 374/53; 374/102; 73/78; 73/803; 73/577
[58] Field of Search ........................ 364/505–508, 364/512, 550, 551.02, 552, 468, 469, 476, 477; 73/78, 763, 767, 768, 801, 803, 573, 577, 634; 340/665, 680; 374/45, 53, 54, 102, 103

[56] References Cited

U.S. PATENT DOCUMENTS

| 4,515,545 | 5/1985 | Hinrichs et al. | 364/508 |
| 4,538,467 | 3/1985 | Stoll | 73/803 |
| 4,566,806 | 1/1986 | DeBondt | 374/53 |
| 4,604,706 | 8/1986 | Fisher, Jr. et al. | 364/507 |
| 4,715,726 | 12/1987 | Tsuruta | 374/53 |

FOREIGN PATENT DOCUMENTS 736002  5/1980  U.S.S.R. ............................. 364/508

Primary Examiner—Parshotam S. Lall
Assistant Examiner—Brian M. Mattson
Attorney, Agent, or Firm—Oblon, Spivak, McClelland, Maier & Neustadt

[57] ABSTRACT

A method for predicting and controlling the strength development of concrete includes placing test concrete having the same composition as the subject concrete in a vessel which may be temperature regulated. The temperature inside the vessel is measured and recorded in a data memory and a data processor. The data is transmitted either in real time or from the data memory and data processor by way of a data transmission line to a temperature regulator for regulating the temperature inside the vessel. The temperature history of the test concrete can then simulate the temperature history of the reference concrete. The strength of the test concrete is measured at different times and the strength data of the test concrete is collected, processed and interpreted. A vessel for receiving the test concrete, a temperature regulator, a temperature controlling unit, a data recorder, a data transmitter and a computer are included.

13 Claims, 17 Drawing Sheets (a)

(b)

(a)

(b)

(c)

METHOD FOR PREDICTING AND CONTROLLING THE STRENGTH DEVELOPMENT OF CONCRETE AND APPARATUS THEREFOR

This application is a Continuation of application Ser. No. 07/116,726, filed on Nov. 4, 1987, now abandoned.

BACKGROUND OF THE INVENTION

1. Field of the Invention

The present invention relates to a method for controlling the strength development of concrete, more particularly, predicting and controlling the strength development of concrete which undergoes special heat history, such as high and low temperatures. The present invention also relates to an apparatus for controlling the strength development of concrete.

2. Prior Art

Generally, relatively large concrete constructions called "mass concrete" tend to show higher temperatures of concrete after placement or deposition than ordinary concrete constructions. This tendency is more clear in the inside of the concrete constructions. In such mass concrete constructions, therefore, it is expected that strength development of the concrete at early ages becomes very high and that undesirable phenomena could occur which would adversely affect the strength of the concrete, such as cracking due to temperature differences between the environment and the mass concrete or within the inside of the mass concrete. Accordingly, the state of the strength development of concrete must be predicted and controlled appropriately by constructors.

When concrete constructions are being constructed under extraordinary or severe enforcement conditions, such as enforcement in hot and cold seasons, the strength development of concrete is greatly different from that of concrete constructions enforced under normal or mild conditions. Therefore, it is necessary to appropriately predict and control the state of strength development of concrete as stated above.

Conventional methods for determining the state of the strength development of mass concrete depending on the temperature history thereof include the following two major methods.

One of them is to collect at various times samples from actual size test concrete of the same composition as that of concrete to be used in an expected concrete construction. The test concrete was placed in water or air on the spot or placed in a standard water container kept at 20° C., and the samples tested as by coring or core extraction experiments were performed to determine the strength of the test samples. This conventional method is disadvantageous especially when the concrete construction undergoes a special temperature history in that the great difference between the concrete construction and the test concrete lowers the accuracy of the method with the result that appropriate control of the strength development is difficult.

Another method is to determine the strength of concrete using a control system for controlling the strength of mass control as shown in FIG. 1. In FIG. 1, reference numeral 1a designates an actual mass concrete, i.e. an actually deposited concrete construction, and 1b is a heat evolution and heat conduction simulation system. The heat evolution and heat conduction simulation system 1b was made based on the supposition that if a one-dimensional rod model of concrete in the direction of the minimum size of the member is set up as shown in FIGS. 2a and 2b where C1 designates an imaginary concrete rod and boundary conditions at the time of construction, such as shuttering or exposition, are given as is on the both ends thereof followed by allowing concrete for heat evolution due to hydration of concrete and heat conduction or heat transfer, the model of concrete can automatically represent chronological temperature variation or temperature distribution in the direction of the minimum size of the member in the concrete. That is, if the above model can be materialized predictors of chronological temperature variation and temperature distribution in the direction of the minimum size of the member are directly available without performing experiments on various characteristics of concrete, such as the amount of heat evolution due to hydration, rate of heat evolution, heat conduction, heat transfer, etc.

A heat evolution and heat conduction system has already been proposed as described in Japanese Laid Open Patent Application No. 60-57252, which has a construction as shown in FIGS. 3 and 4. That is, concrete to be tested is deposited in an insulated tank 2 to form a concrete rod 3 having a cross-section of about 30 cm×30 cm. Proportional plus integral plus derivative action (P. I. D. Action) is performed so that the internal temperature of the concrete rod and the temperature conditions of the four surrounding surfaces of the insulated tank can coincide with each other. The temperature control is performed by a temperature control device 4 which measures the internal temperature of the concrete rod 3 using a plurality of C—C thermocouples 5 and sends instructions to a plurality of control heaters and heat transfer plates 6 in the four-sided insulated tank 2 so that they can always establish in real time the same temperature conditions as those detected.

With the above construction, there is formed in the four-sided insulated tank 2 a state in which heat conduction and heat transfer from the concrete rod in the direction of the surrounding 4 walls does not occur. Therefore, the concrete placed in the insulated tank 2 shows heat evolution due to hydration and heat conduction and heat transfer in the longitudinal direction (in the direction of the minimum size of the member).

As a result, automatic simulation of the heat evolution of mass concrete members due to hydration and heat conduction and heat transfer in the direction of the minimum size of the member is obtained. Predictors of chronological temperature variation and temperature distribution in the direction of the minimum size of the member can be obtained directly experimentally.

Reference numeral 1c designates a strength development control system for mass concrete, which comprises a control box 1d including a display device $1d_1$ for displaying the temperature or temperature difference, a temperature control device $1d_2$, etc., a water tank 1e adapted to place therein a test concrete member 1f, a thermocouple 1g for feeding back the temperature information and a heating unit 1h including a heater (not shown) for heating the test concrete member 1f and a fan (not shown), both the thermocouple 1g and the heating unit 1h being placed in the water tank 1e. In the thus-constructed control system 1c for mass concrete, the predictors of the temperature of the members output from the heat evolution and heat conduction simulation system 1b are obtained by the control device $1d_2$ in the control box 1d. The control device $1d_2$ automatically sends instruction to the heating unit 1g to enable it to give the same temperature conditions as the determined temperatures of the test concrete members 1f in real time, and as a result predictors of the state of the strength development of mass concrete members which are exposed to an unsteady high temperature state at early times can be obtained from the test concrete members in the water tank 1e.

The control system 1c can be operatively connected to C—C thermocouples embedded in an actually deposited mass concrete member at an appropriate interval to collect data on the temperature of the actually constructed mass concrete in order to use the data in the control of the strength development upon actual construction.

However, the above described conventional methods and apparatus are disadvantageous because the first method requires large-scale experiments which involve high costs. According to the second method, a large number of thermocouples must be arranged over a long distance sometimes as long as several hundred meters for large-scale constructions, such as a nuclear power plant and the like, and also because it is necessary to deposit concrete in the heat evolution and heat conduction system for giving the temperature process of mass concrete, which limits the conditions of experiments. Further, the conventional methods are also disadvantageous in that it was difficult to obtain accurate information on the temperature of concrete deposited in a long distance from the place of prediction and control especially when obstructions such as sea and rivers are present between the place of prediction and control of the strength development and the place of actual deposition of concrete.

SUMMARY OF THE INVENTION

It is an object of the present invention to obviate the defects of the prior art and provide a method for predicting and controlling the strength development of concrete which enables accurate real time prediction and control of the strength development of concrete constructions even when the place where prediction and control is performed is far distant from places where the concrete is actually deposited or information on temperature is handled or stored or even when an obstruction such as sea or river intervenes therebetween.

It is another object of the present invention to provide an apparatus for predicting and controlling the strength development of concrete which can achieve the above-described method of the present invention.

As a result of extensive investigation, it has now been found that the above-described objects can be achieved by the use of a temperature memory means for recording the temperature history of an actually deposited concrete, a data processing means (computer) and a means for transmitting data on the temperature of concrete from the spot to the place or station where the data are processed and the prediction and control of the strength development is performed.

Therefore, the present invention provides a method for predicting and controlling the strength development of a concrete, comprising placing a test concrete member having the same composition as said concrete in a vessel capable of being regulated with respect to the temperature thereof, measuring the temperature inside said vessel, recording said temperature data in a data memory means and a data processing means, transmitting data on the temperature of a reference concrete from said reference concrete in real time or from said data memory means and said data processing means which store data on the temperature of a reference concrete previously obtained via a data transmission means to a temperature regulator for regulating the temperature inside said vessel, regulating the temperature of said vessel based on said data from said reference concrete or from said memory means and said data on the temperature inside said vessel from said memory means so that the temperature history of said test concrete member can simulate the temperature history of said reference concrete, measuring the strength of said test concrete member at different times, collecting data on the strength of said test concrete member, processing said data in said data processing means, and interpreting the results.

Also, this invention provides an apparatus for predicting and controlling the strength development of a concrete, comprising a vessel adapted for placing therein a test concrete member having the same composition as said concrete, a temperature regulating means, a temperature controlling unit arranged in said vessel and operatively connected to said temperature regulating means and adapted for controlling the temperature inside said vessel, a data recording means for recording the chronological change of the temperature of a reference concrete placed at a place other than said vessel, or, a data transmitting means for transmitting data from said reference concrete or from a temperature measuring means for measuring the temperature of a reference concrete a model concrete to said data recording means, a computer operatively connected to said data recording means and adapted for processing or recording the data from said data recording means.

The above method and apparatus of the present invention enable accurate real time prediction and control of the strength development of concrete no matter how far the distance is between the spot where a concrete structure is actually constructed or the place where the information on the temperature of concrete is handled or processed and the place where the strength development is taking place, or even if there is an obstruction such as sea or river therebetween.

BRIEF DESCRIPTION OF THE ACCOMPANIED DRAWINGS

FIG. 1 is a schematical illustration of a conventional system for controlling the strength development of concrete;

FIGS. 2(a) and 2(b) are schematical illustrations of an imaginary concrete rod defined in an actually deposited concrete or a model concrete;

Figure 15:
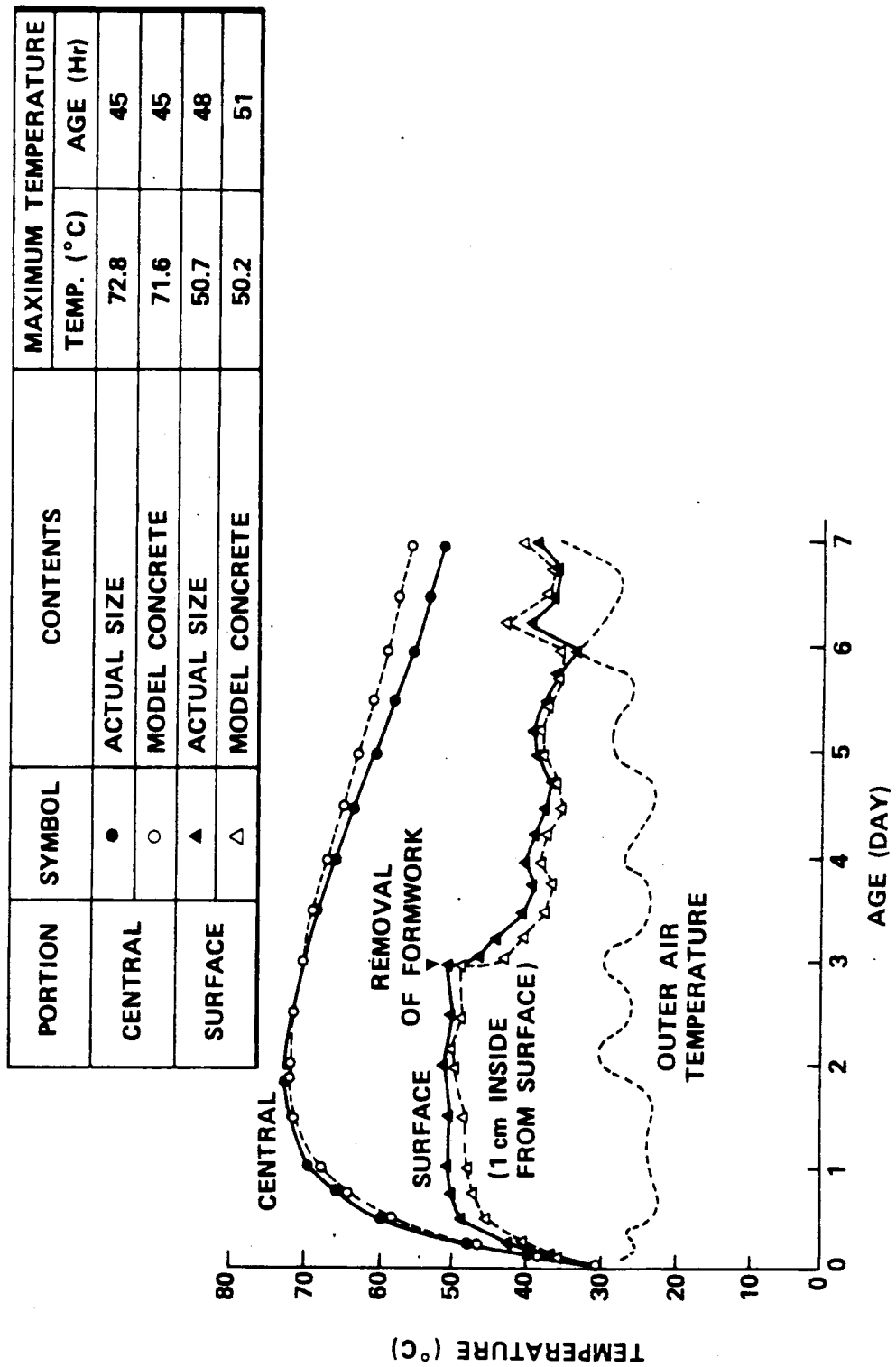
Figure 16:
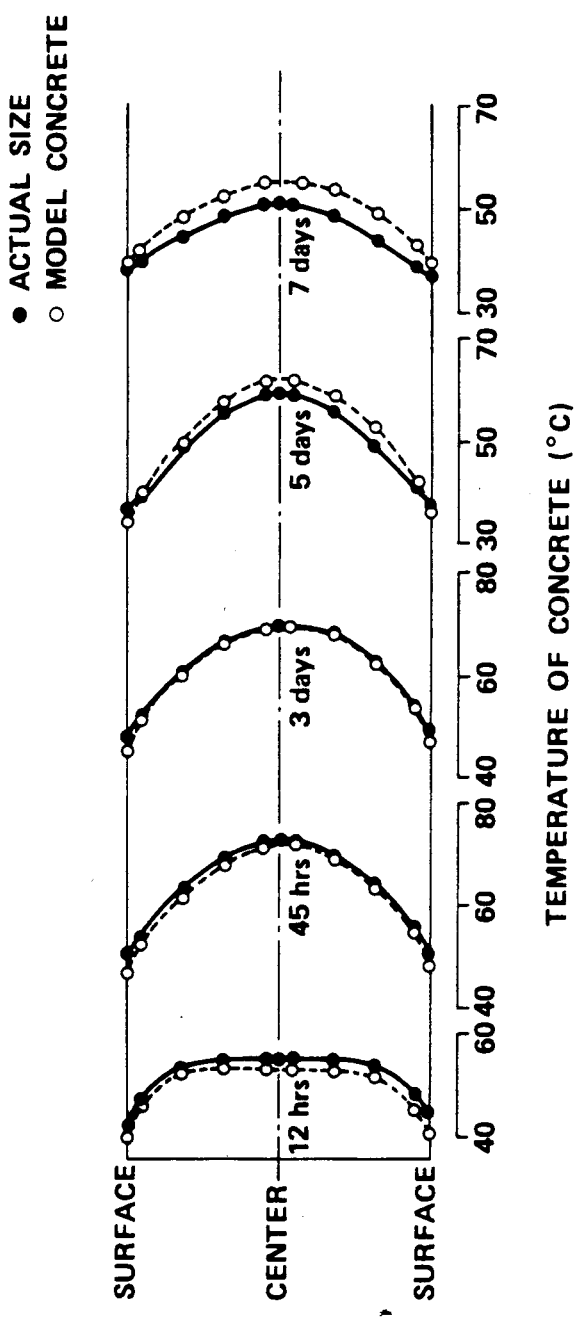
Figure 17:
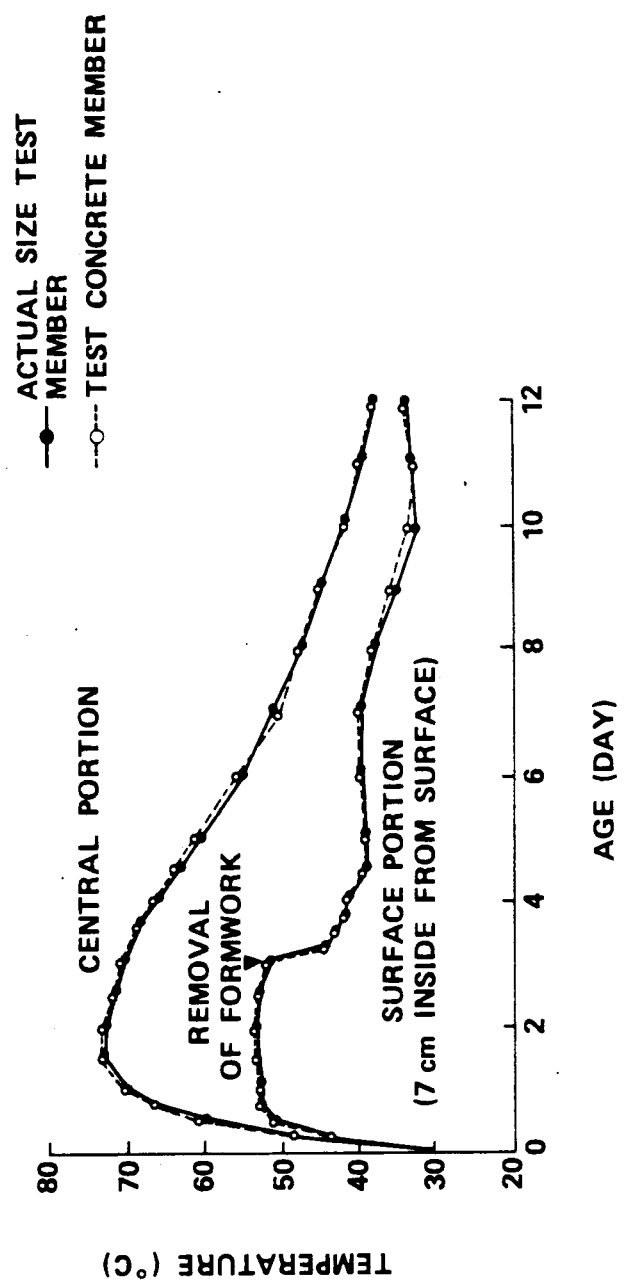
Figure 19:
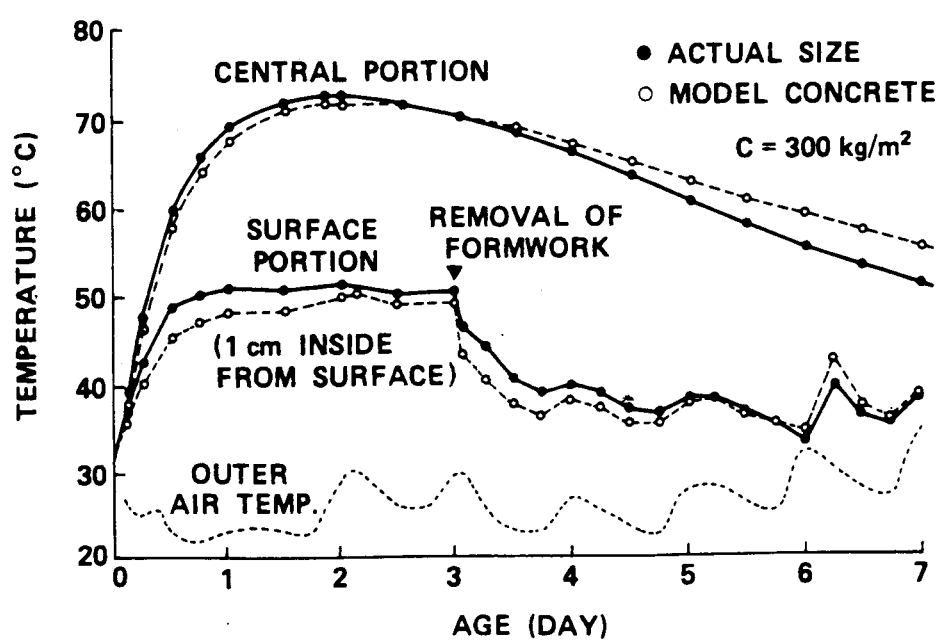
Figure 20:
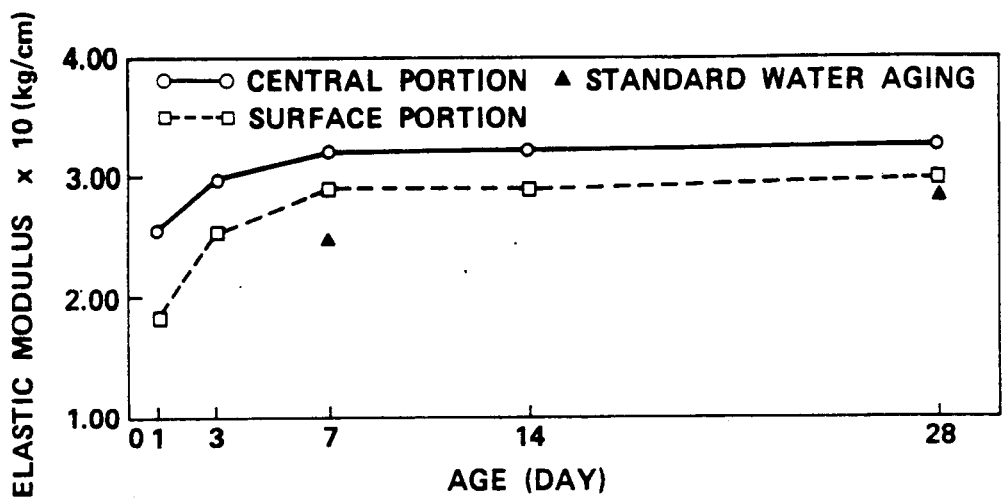
Figure 21:
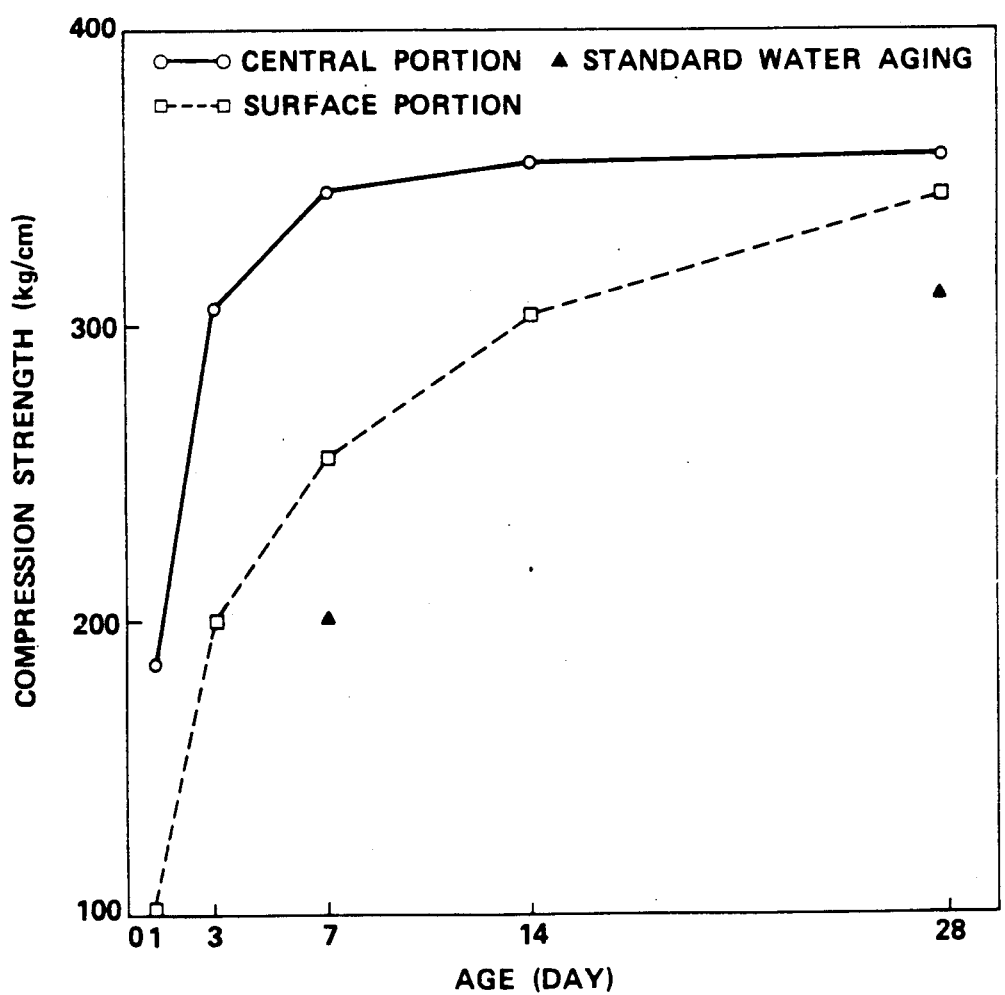
Figure 22:
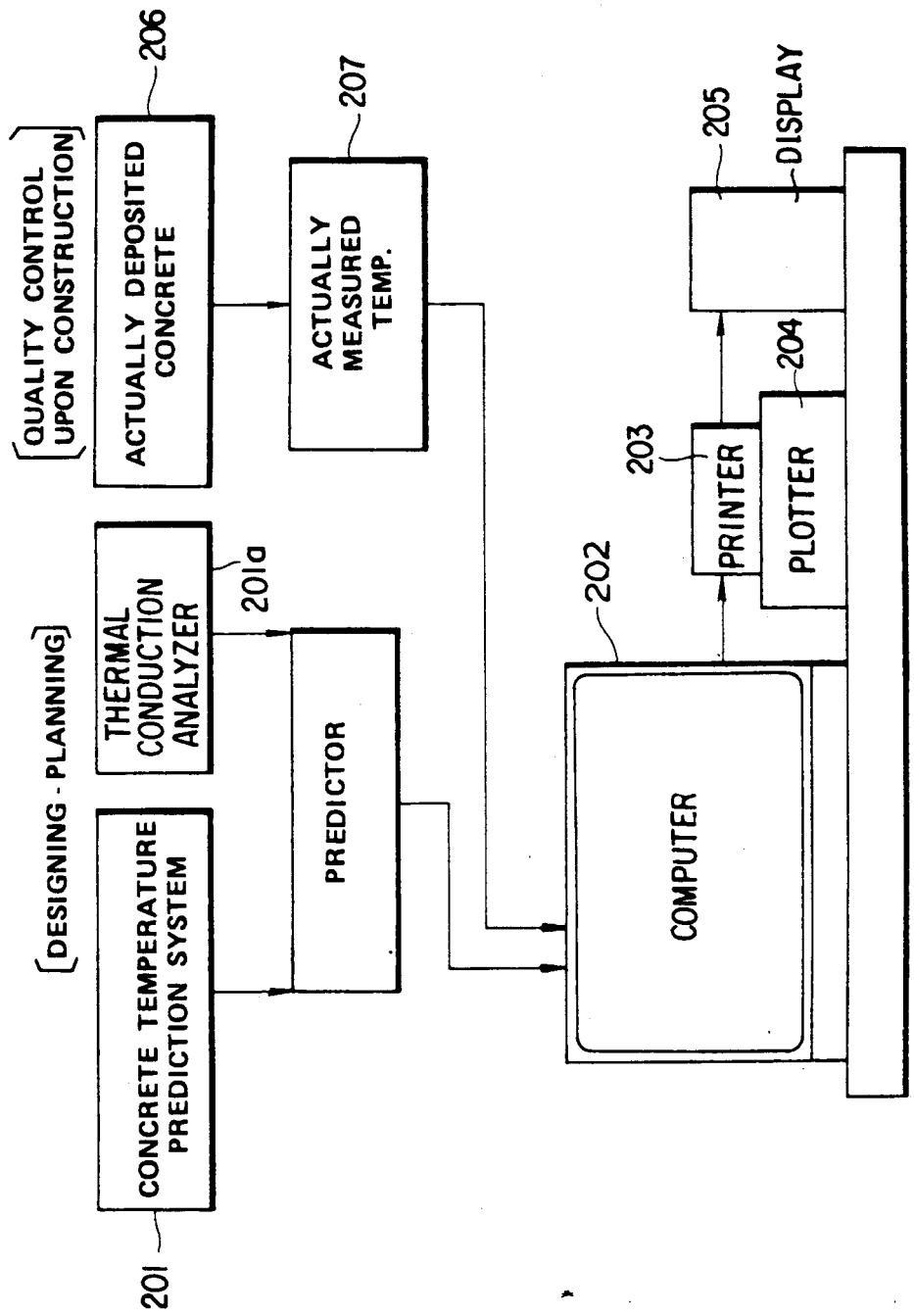
Figure 23:
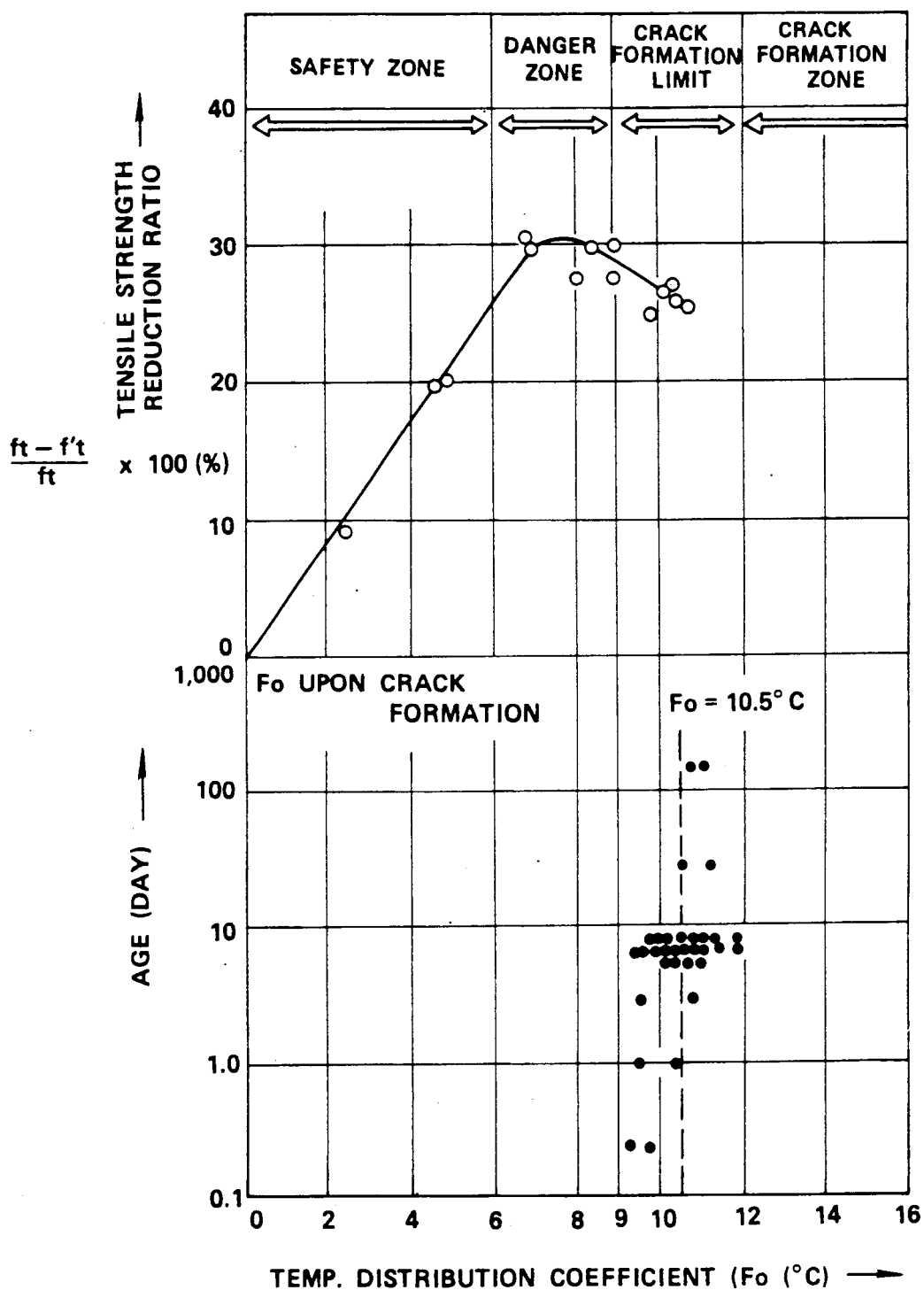
Figure 24:
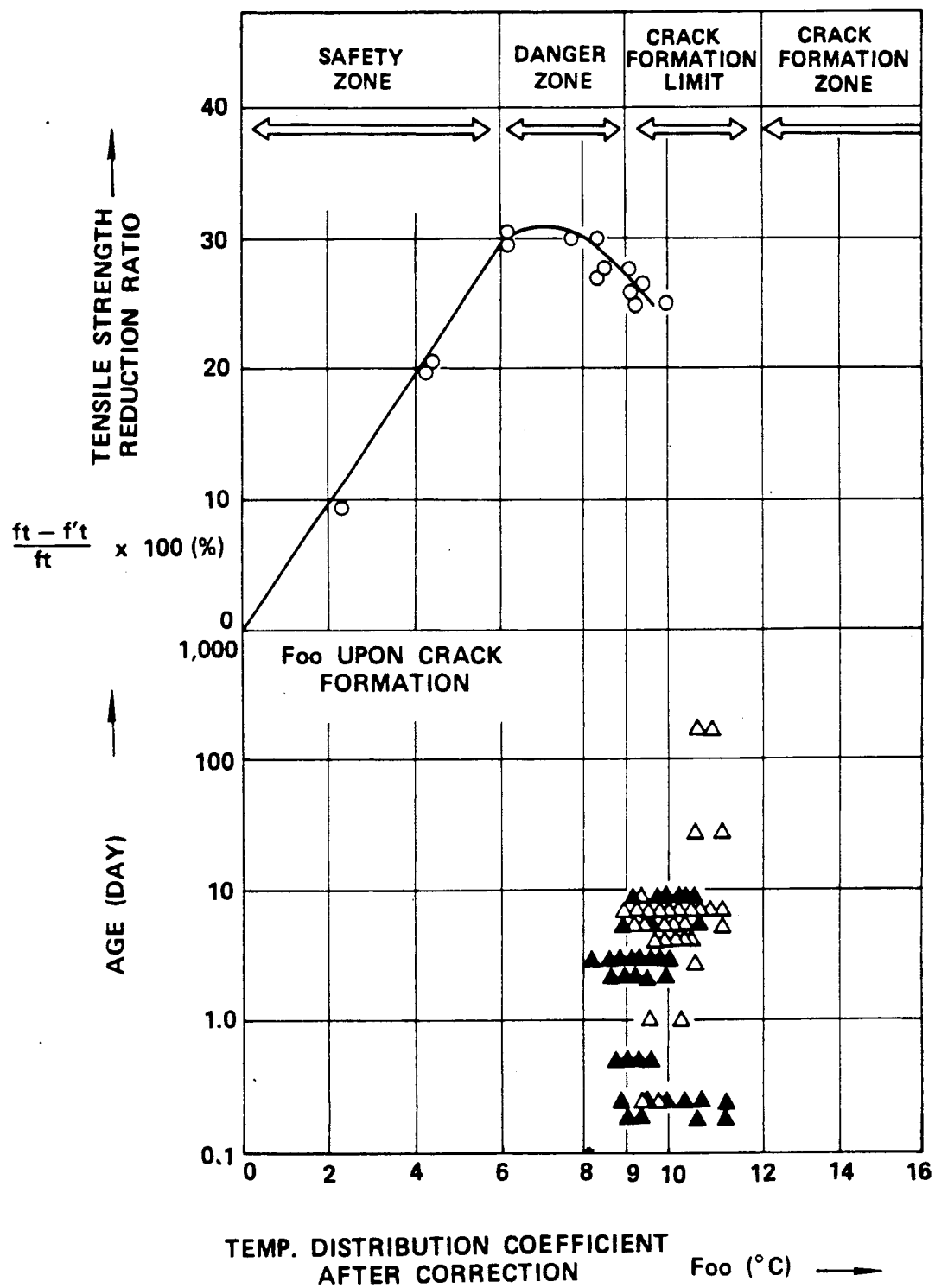
Figure 25:
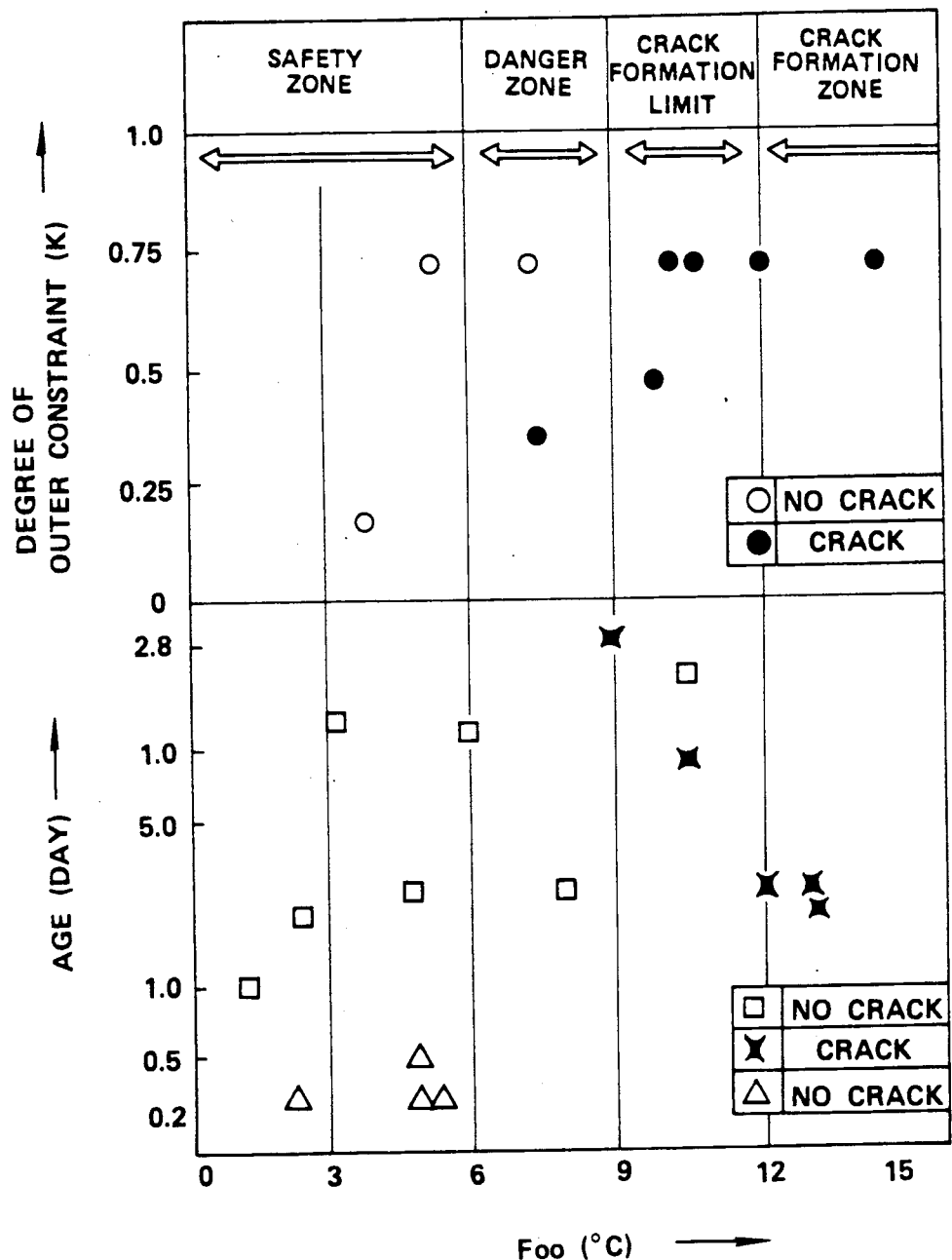

FIGS. 14(a)-(c) are views showing the appearance of the actual size test concrete member used in an example of this invention;

FIG. 15 is a graph showing the chronological temperature variation of the actual size test concrete member and the model concrete used in the example of this invention;

FIG. 16 is a graph showing the temperature distribution in the actual size test concrete member and the model concrete used in the example of this invention;

FIG. 17 is a graph showing the chronological temperature variation of the actual size test concrete member and the model concrete used in the example of this invention;

FIGS. 18a, 18b and 18c are views showing the appearance of the actual size test concrete member used in the example of this invention;

FIG. 19 is a graph showing the chronological temperature variation of the actual size test concrete member and the model concrete used in the example of this invention;

FIG. 20 is a graph showing the chronological change in the elastic modulus of concrete;

FIG. 21 is a graph showing the chronological change in the compression strength of concrete;

FIG. 22 is a block diagram of the prediction and control system of the occurrence of cracks in a mass concrete according to one embodiment of this invention;

FIG. 23 is a graph showing temperature distribution coefficient $F_0$ and the occurrence of cracks;

FIG. 24 is a graph showing temperature distribution coefficient $F_{00}$ and the occurrence of cracks; and FIG. 25 is a graph explaining the state of the occurrence of cracks.

DETAILED DESCRIPTION OF THE INVENTION

Figure 5:
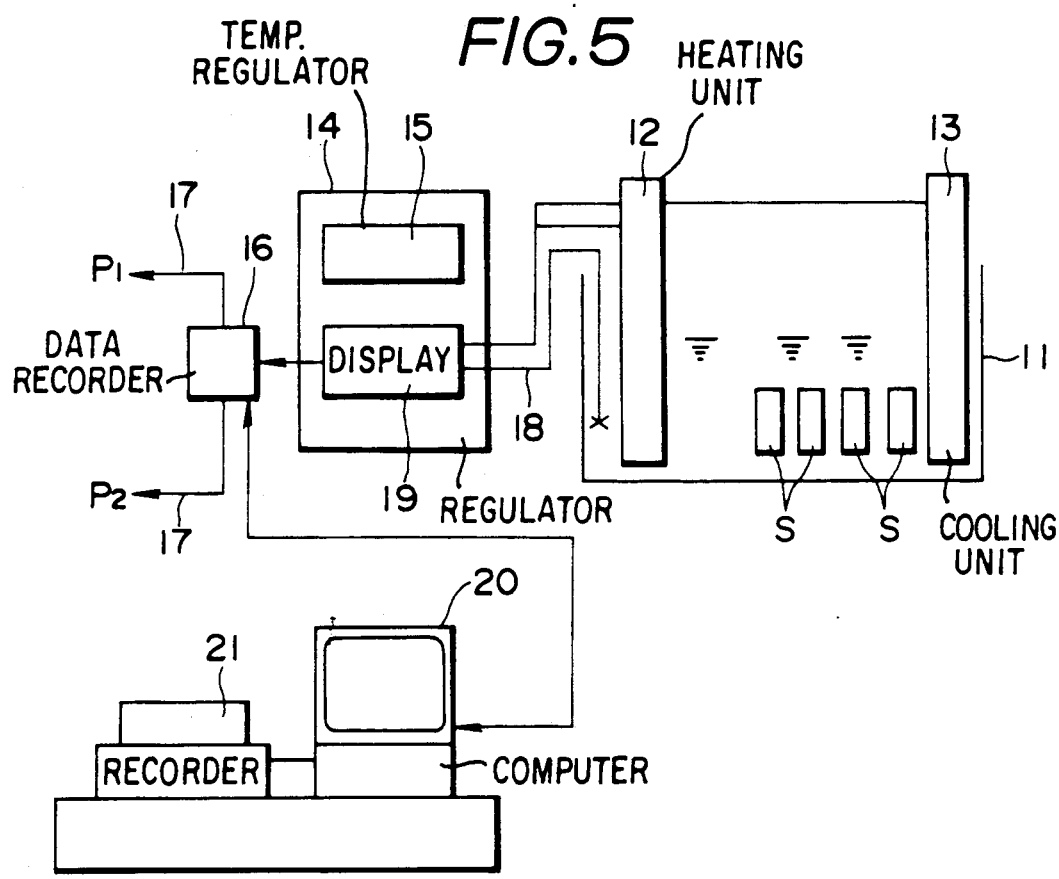
FIG. 5 is a schematical view of the system of predicting and controlling the strength development of concrete according to one embodiment of the present invention.

FIG. 5 shows an embodiment of the apparatus for predicting and controlling the strength development of concrete according to this invention. In FIG. 5, reference numeral 11 designates a vessel which may be a tank which contains a liquid, generally water, in which test concrete members S are placed. Sometimes the vessel 11 need not contain a liquid and the test concrete members may be exposed to air. For simplicity, the following description will be made with respect to the case where a water tank is used. In the water tank 11 are placed a heating unit 12, e.g. a set of an electric heater and a fan, and a cooling unit 13, e.g. a set of a brine pipe and a refrigerator, so that they can be submerged in the water in the tank 11. The heating unit 12 and the cooling unit 13 are operatively connected to a regulating box 14 comprising a temperature regulator 15 which regulates the units 12 and 13. The regulator 15 is operatively connected to a data recorder or temperature memory means 16, which is operatively connected to a plurality of thermocouples 17, e.g. C—C thermocouples, embedded at appropriate positions P1 in an actually deposited concrete or P2 in a model concrete imitating the actually deposited concrete as a means for detecting the temperature thereof and obtaining the chronological change of the temperature of the actually deposited concrete or the model concrete. The thermocouples 17 send signals corresponding to the detected temperature history to the data recorder which records the signals in its memory and at the same time sends the signal on the temperature history to the temperature regulator 15, which regulates the heating and cooling units 12 and 13, respectively, to control or adjust the temperature of the water in the water tank 11 so that the temperature of the water coincides with that temperature history data. For this purpose, a thermocouple 18, e.g. a C—C thermocouple, placed in the water tank 11 is operatively connected to the temperature regulator 15. The state of the temperature regulation by the temperature regulator 15 is displayed on a temperature display device 19 equipped in the regulating box 14. Reference numeral 20 designates a computer (or a temperature memory means), which records the signals on the temperature history of the actually deposited concrete or model concrete sent from the data recorder 16 and at the same time regulates the entire system of the apparatus for predicting and controlling the strength development of concrete according to the present invention. Reference numeral 21 designates an output device such as a printer, a plotter, etc. for outputting the data recorded in the computer 20 in which is stored not only data on the actually deposited concrete but also data on the temperature history of previously deposited or fabricated concrete that resembles the actually deposited concrete with respect to various conditions. The transmitting means may be an optical fiber transmission system, a wireless telecommunication means, a telephone system or telephone circuit, a light transmission system such as a laser beam transmission system, etc. For example, if a telephone circuit is used as the transmission means, it may be operated continuously or intermittently at desired time intervals.

Figure 7:
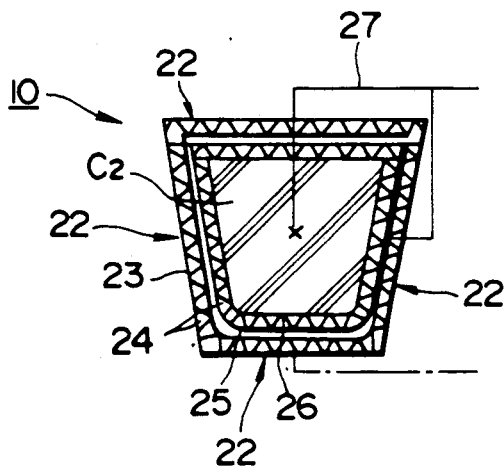
FIG. 7 is a cross-sectional view of the temperature prediction device shown in FIG. 6.
Figure 6:
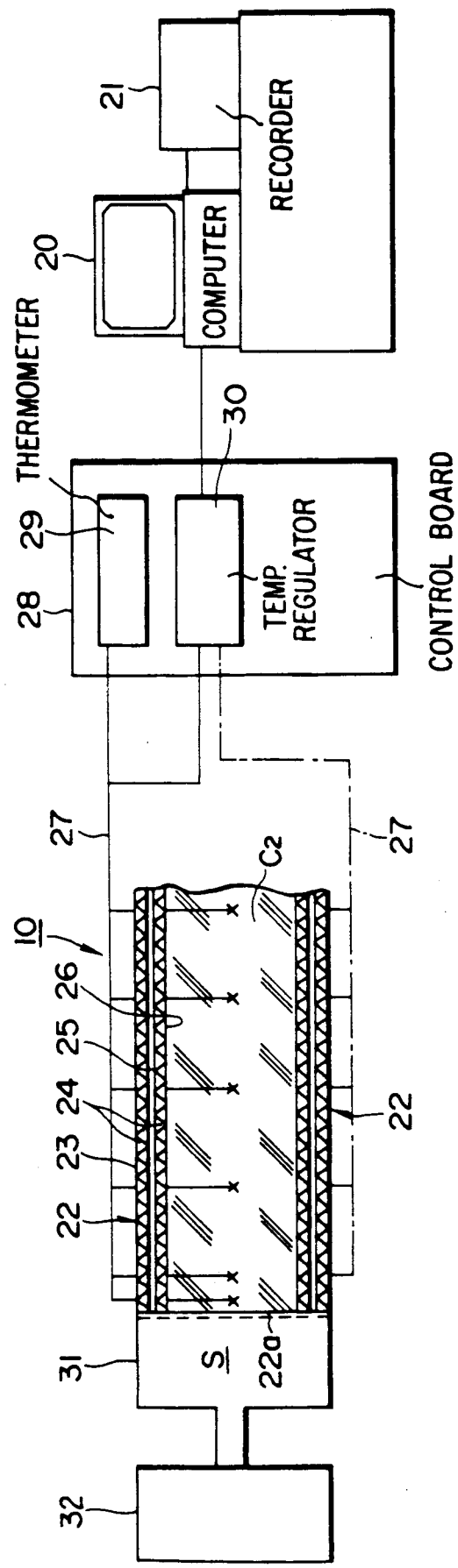
FIG. 6 is a diagrammatical view of the temperature prediction device according to one embodiment of this invention.

As shown in FIGS. 6 and 7, a model concrete $C_2$ having the same composition as that of a concrete to be deposited actually is deposited in a four-sided insulated tank 22.

Figure 1:
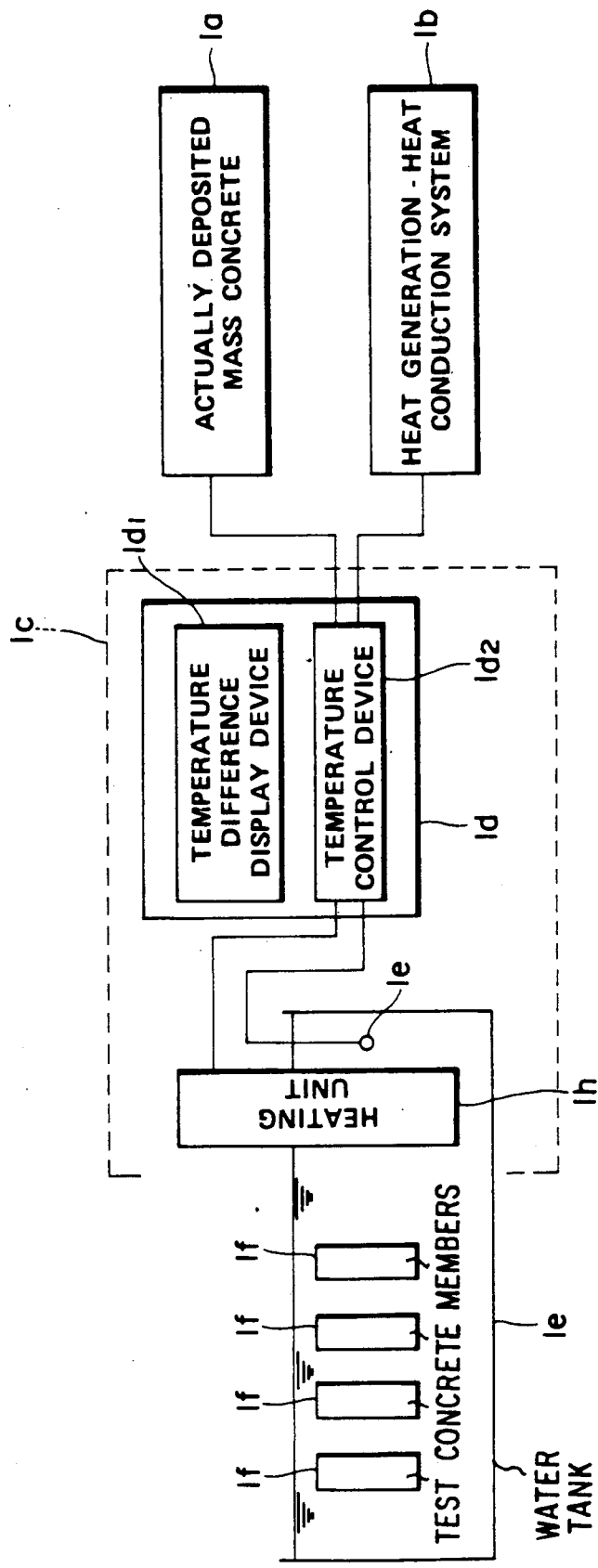
Figure 2:
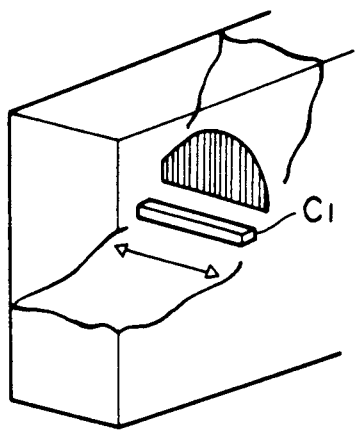
Figure 2:
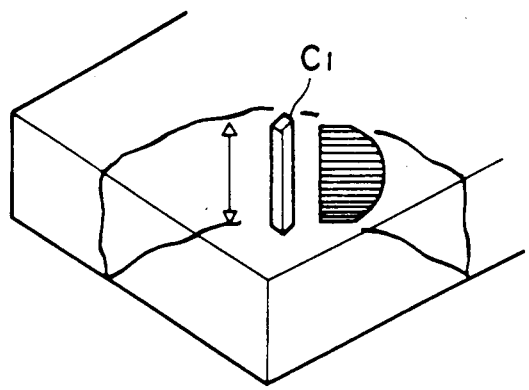
Figure 3:
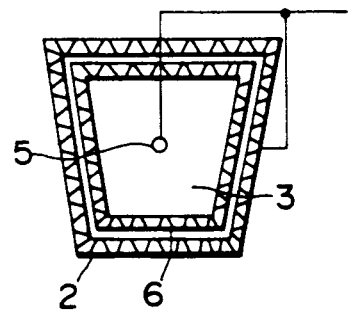
FIG. 3 is a cross-sectional view of an insulated tank which can be used in the present invention.
Figure 4:
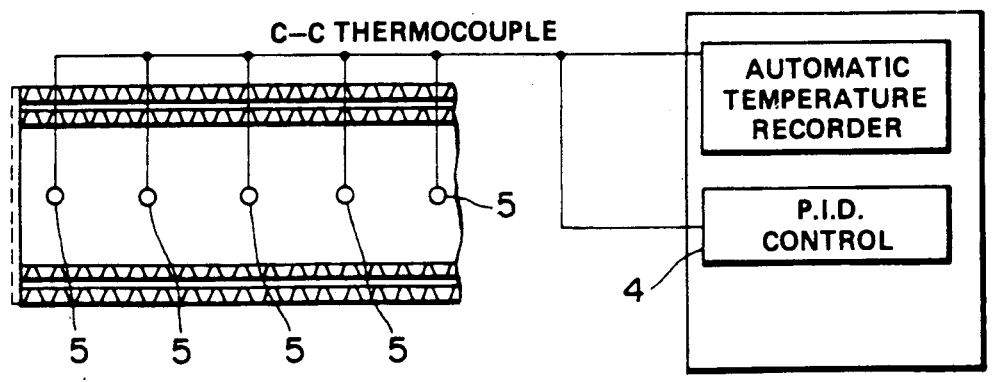
FIG. 4 is a schematical illustration of the insulated tank and related apparatus which can be used in the present invention.

This is intended to simulate the thermal behaviors of a concrete such as the heat evolution as a result of hydration, heat conduction, heat transfer, etc. in the direction of the minimum thickness of the actually deposited concrete. This is based on the supposition that a rod concrete member is taken out from an actually deposited concrete C along the minimum thickness thereof and complete heat insulated conditions are given around the four peripheral surfaces thereof with the exception of both end surfaces, the length which are left uninsulated as shown in FIGS. 2A and 2B. By so doing, it is intended to obtain predictors of a one-dimensional change in temperature or of the state of temperature distribution. The same explanation as to FIGS. 2A and 2B with respect to the conventional system is applicable here.

For this purpose, the four-sided insulated tank comprises a steel formwork 23 which is constructed so as to be open at both ends along the length thereof. Inside the steel formwork 23 is provided a heat insulating board 24 of glass wool, a heater 25 for regulating the temperature inside the tank 22 which heater is combined with a heat conducting board, and an FRP (fiber reinforced plastics) board 26. The glass wool heat insulating board 24 serves to reduce exchange of heat between the insulated tank and the outside and keep the inside of the insulated tank in a diabatic state with the heater 25 compensating for the heat which is lost through the steel formwork 23.

A plurality of thermocouples 27 are arranged inside the concrete member $C_2$ or near the surface thereof in the longitudinal direction. The thermocouples 27 are connected to a control board 28 which is placed adjacent to the insulated tank 22 and has connected thereto a self-recording thermometer 29 and a temperature regulator 30. The temperature regulator 30 regulates the heater 25 appropriately according to the signals detected by the thermocouples. The reference point temperatures of the model concrete $C_2$ are input through the self-recording thermometer 29 in the data recorder 16 as temperature history data. The reference point temperatures are temperatures of predetermined points or sites, such as the inside and surface of the model concrete $C_2$ measured by the thermocouples 27, and the reference points are selected appropriately depending on the kind of concrete to be actually deposited.

Preferably, each of the ends of the four-sided insulated tank 22 are covered with a casing 31 so as to cover or seal the opening 22a to form a temperature control space $S_T$. In the casing 31 there can be provided a regulator 32 for regulating the temperature of the inside of the casing 31. A suitable example of the regulator 32 is an air-conditioner (not shown) which is adapted to send warm or cool air to the inside of the casing 31 or more specifically into the temperature control space $S_T$ to regulate the temperature thereof and give the end surface of the model concrete which corresponds to the end in the direction of the minimum thickness of the actually deposited concrete a temperature condition, and more specifically the temperature of air in the temperature control space $S_T$ which corresponds to the condition of the actually deposited concrete such as use of a plywood or metal form or exposure to air. With this procedure the chronological change and temperature distribution of the concrete in the direction of the minimum thickness of the concrete member is shown in FIGS. 2A and 2B.

Hereinafter, the method of predicting and controlling the strength development according to an embodiment of this invention will be described.

At the stage of designing or planning the construction, at first various construction conditions such as those as to whether the concrete to be deposited will be exposed to air or be covered and whether plywood or metal form is to be used to cover the surface of the concrete are determined followed by testing with the above-described temperature prediction system. That is, the temperatures of the model concrete $C_2$ having the same composition as that of the concrete to be actually deposited for the construction of a mass concrete structure at appropriate reference points $P_2$ thereof as shown in FIGS. 6 and 7 are measured by means of the thermocouples 27. The chronological changes of the temperatures of the reference points $P_2$ are transmitted via an appropriate transmission means (not shown) such as a telephone system, an optical fiber system, a wireless transmission system, etc., and recorded in the data recorder 16 as temperature history data. On the other hand, the temperature history data are also recorded in the computer 20. Preferably, this procedure is repeated in order to collect and record various temperature history data under different conditions of concrete deposition.

Then, the test concrete members S are placed and submerged in water in the water tank 11, and the heating unit 12 and the cooling unit 13 are regulated by the temperature regulator 15 so that the temperature of the water in the water tank 11 can be changed in accordance with a selected one of the various temperature history data recorded in the data recorder 16 or the computer 20. As the result, the test concrete members S undergo substantially the same temperature conditions as those of a model concrete $C_2$ or previously deposited concrete. At predetermined times, the test concrete members S are taken out from the water tank 11 and subjected to examination for their strength. The results obtained are used for the prediction of the strength development of an actually deposited concrete C having the same composition as the model concrete. The temperature history data and the chronological change of the temperature the water in the water tank 11 is automatically displayed in real time on the display device 21 in the form of a graph.

On the stage of actual deposition of a concrete, the temperature history data from the appropriate reference points $P_1$ are transmitted via a data transmission means such as a telephone system, an optical fiber transmission system, a wireless telecommunication system, etc. and recorded in the data recorder 16 or the computer 20. The data are on the one hand compared by the computer 20 with the temperature history data of the model concrete $C_2$ collected on the stage of designing and on the other hand sent to the temperature regulator 15, which regulates in real time the temperature of the water tank 11 in accordance with the temperature history data of the actually deposited concrete C. Therefore, the test concrete member S encounter substantially the same temperature conditions as those under which the actually deposited concrete is left, thereby enabling the control of the strength development. The computer 20 is programmed so as to issue a warning signal when the difference between the temperature history data of the actually deposited concrete and those of the model concrete $C_2$ exceeds a predetermined level and therefore a reduction in the strength of the actually deposited concrete C is expected.

The above described method and apparatus make it possible to give the test concrete members S the temperature conditions of the actually deposited concrete C or the model concrete $C_2$ directly and exactly, with the result that the prediction and control of the strength development of the actually deposited concrete C can be performed directly and with ease and precision without presumption or predictory calculation.

The prediction and control system of this invention is advantageous in that since the temperature history data of the actually deposited concrete C and those of the model concrete $C_2$ temporarily recorded in the data recorder 16 the data can be stored or processed independently of the temperature regulator 15. In other words, the data may be handled in an off-line state with respect to the temperature regulator 15, i.e. the temperature measurement step may be operated independently of the strength development control apparatus. Therefore, collection of temperature history data of various concrete compositions can be carried out prior to the operation of the control of the strength development of the concrete, and the control of the strength development of concrete can be performed under various temperature conditions. Further, provision of the cooling unit in the water tank enables the simulation of concrete deposited in cold or winter seasons or at chilly or icy areas, thus broadening the field of application of the method and apparatus of this invention. Another advantage of the system of this invention is that the processing of the data on the actually deposited concrete and control operation of the strength development of the actually deposited concrete can be performed in real time and despite the presence of intervening obstructions, such as sea, river, etc.

According to a preferred embodiment of this invention, the temperature history data of a model concrete or those of a previously actually deposited concrete are stored in a data memory means, which data then are read out with a reading out means and sent to a temperature regulator to give test concrete members the same temperature conditions as the model concrete or actually deposited concrete.

Figure 8:
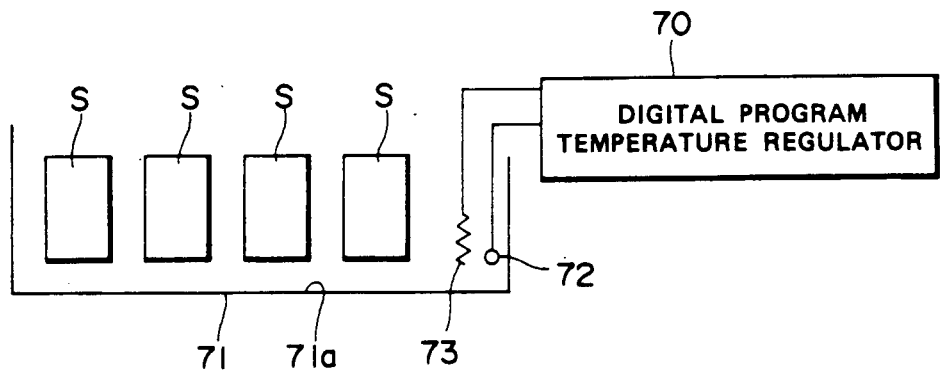
FIG. 8 is a diagrammatical view of the apparatus for the prediction and control of the strength development of concrete according to one embodiment of this invention.
Figure 9:
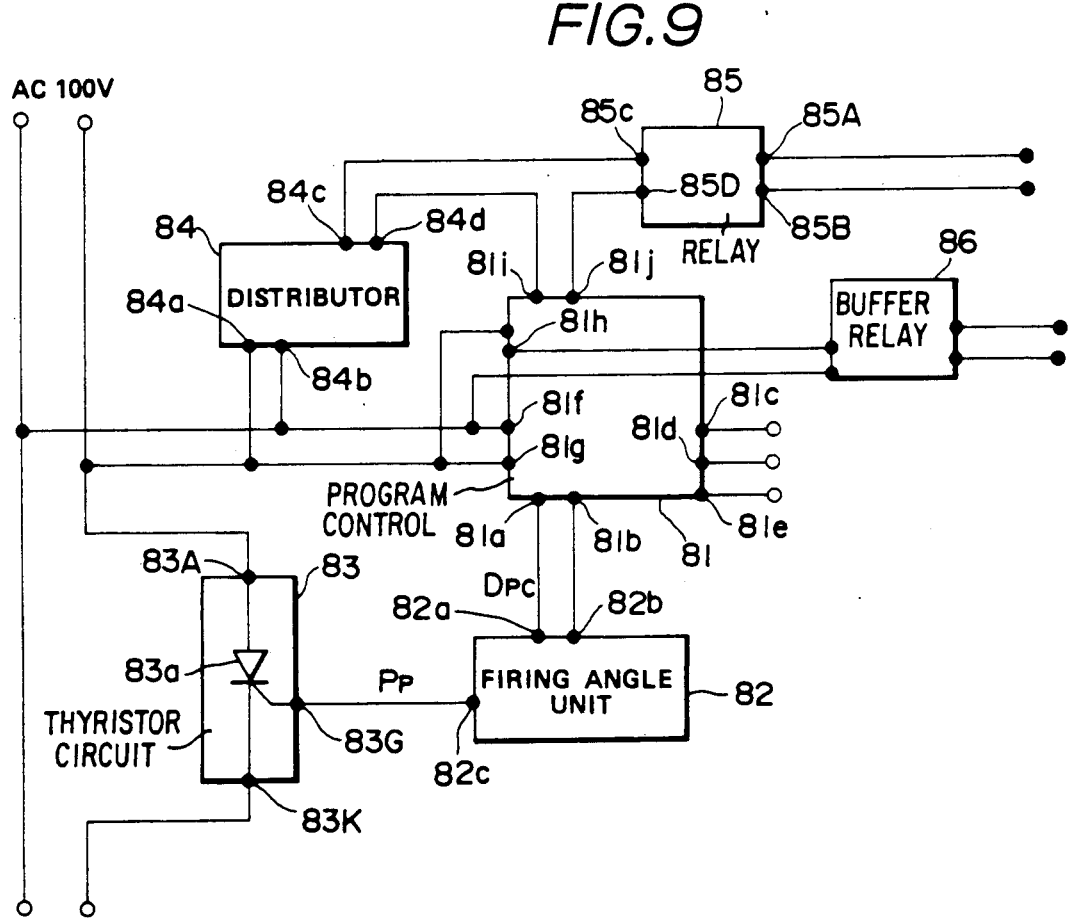
FIG. 9 is a block diagram showing the digital program temperature regulator according to one embodiment of this invention.
Figure 10:
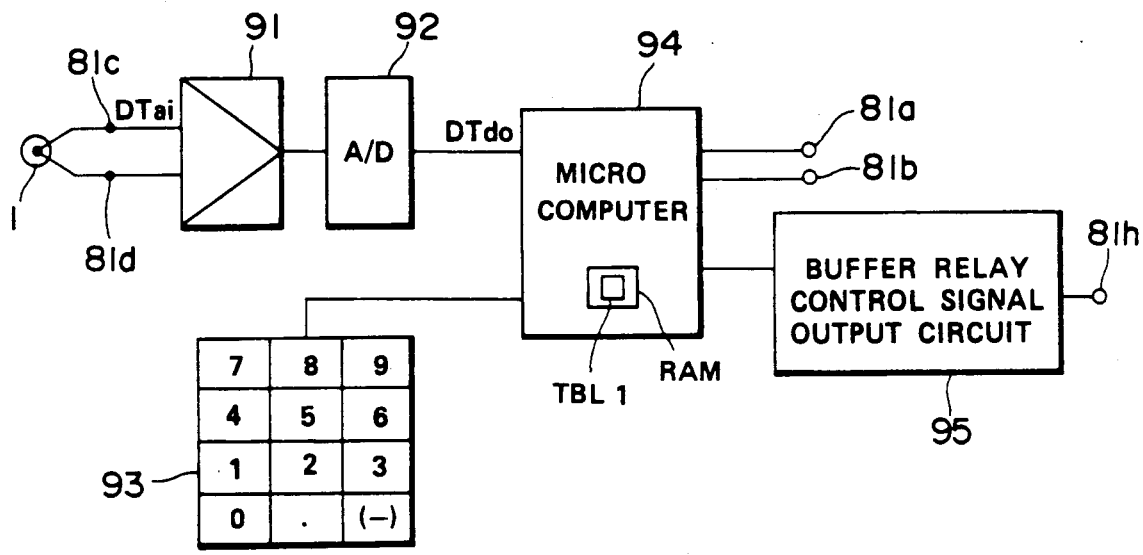
FIG. 10 is a block diagram showing the construction of the digital program temperature regulator according to one embodiment of this invention.
Figure 11:
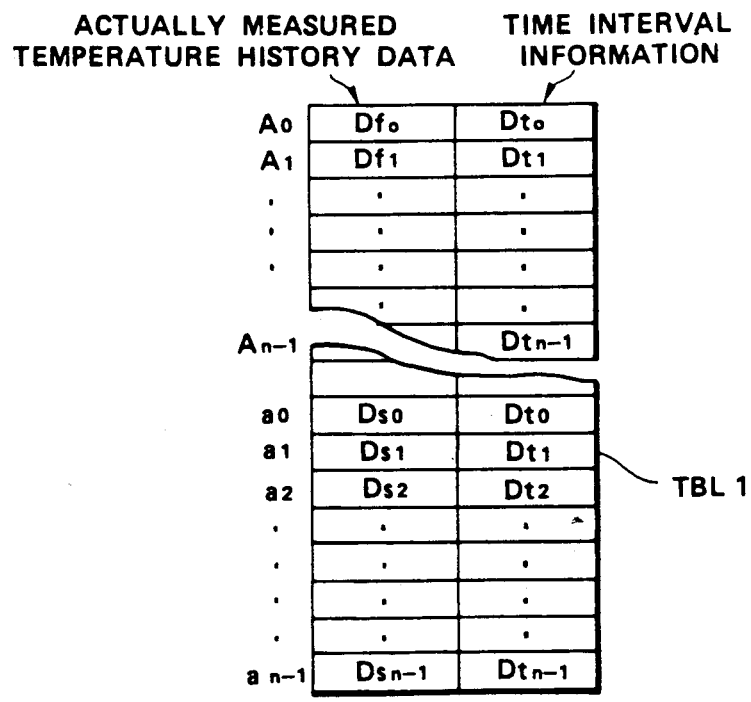
FIG. 11 shows a data table set up in the microcomputer used in the digital program temperature regulator shown in FIGS. 8 to 10.
Figure 12:
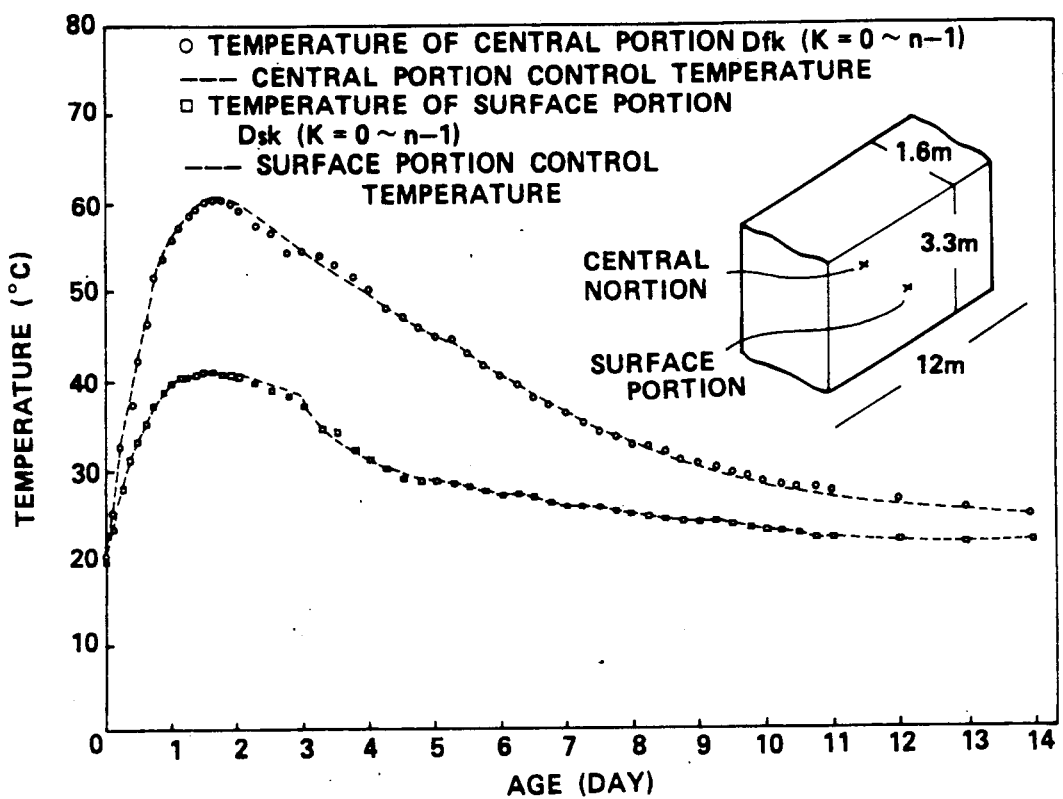
FIG. 12 is graph showing temperature history curves of a mass concrete at a surface portion and a central portion thereof.

FIG. 8 is a block diagram showing an embodiment of this invention. In FIG. 8, reference numeral 70 designates a digital program temperature regulator which has a construction shown in FIG. 9 in which reference numeral 81 designates a program control which is provided with output terminals 81a and 81b, terminals 81c, 81d and 81e to which platinum resistors (thermocouples) for feeding back temperature information are connected, input terminals 81f and 81g for charging alternating current, a triode AC switch (TRIAC) 71h for regulation, time signal output terminals 81i and 81j, etc. More particularly, the program control 71 is of the construction as shown in FIG. 10. That is, the program control 71 comprises an amplifier circuit 91 for amplifying analog signal DTai corresponding to the information on temperature being fed back from the temperature sensors such as thermocouples, an A/D converter circuit 92 which converts the output signal DTao into digital signal DTdo and input the latter to a microcomputer 94, a keyboard 93 for the input and output operations of the data, a buffer relay control signal output circuit 95 and the like. The microcomputer 84 may comprise a conventional memory device such as CPU, RAM, ROM, I/O interface, etc. In the RAM provided in the microcomputer 94 is set up a data table TBL 1 as shown in FIG. 11. In TBL 1, there is stored in continuous address $A_0$ to $A_{n-1}$, $a_0$ to $a_{n-1}$ actually measured data $Df_0$ to $Df_{n-1}$ of temperature history curve for the central protion of, e.g. a mass concrete (a concrete beam with a minimum thickness of 1.6 m) as shown in FIG. 12 and actually measured data $Ds_0$ to $Ds_{n-1}$ of temperature history curve for the surface portion of the above-described mass concrete together with time interval information data $Dt_0$ to $Dt_{n-1}$. These actually measured data can be input by means of the keyboard 93.

The time interval information data $Dt_k$ is a time interval information for up to the next actually determined data $Df_{k+1}$. For this reason, the shorter the time interval, the greater the rate of change in the temperature history curve, with the result that the approximation error of the curve can be reduced.

Referring back to FIG. 9, reference numeral 82 designates a firing angle unit, which is constructed so as to receive serial firing angle control signal Dpc from the program control 81 and output phase control pulse Pp which corresponds to the signal Dpc and is synchronized with zero cross of AC 100 V and 50 Hz.

Reference numeral 83 designates a thyristor circuit, which comprises a thyristor 83a, and terminals 83A, 83K and 83G connected to the anode, cathode and gate, respectively, of the thyristor 83a. The terminal 83A is connected to an alternating current source of AC 100 V, and the terminal K is connected to a heater shown in FIG. 8.

Reference numeral 84 designates a distributor provided with a regulator for converting an alternating current of AC 100 V into a direct current of DC 24 V, and for this purpose the distributor 84 comprises input terminals 84a and 84b for inputting the alternating current AC 100 V from the alternating current source and output terminals 84c and 84d for outputting the direct current DC 24 V.

Reference numeral 85 designates a relay of DC 24 V which outputs a time signal by on-off operation of a-contact terminals 85A and 85B. 85C and 85D are coil terminals of the relay 85.

Reference numeral 86 designates a buffer relay (AC 100 V relay) which can output a warning signal by the on-off operation of a-contact in the same manner as the relay 85.

Referring back to FIG. 8, reference numeral 71 designates a vessel provided with a C—C thermocouple 72 which is a temperature sensor arranged on a right-hand side wall of the vessel 71 at a little lower position and adapted for feeding back the temperature information inside the vessel 71. The thermocouple 72 is connected to the terminals 81c and 81d of the program control 81.

Reference numeral 73 designates a heater load connected between the terminal 83K of the thyristor circuit 83 and the common of the alternating current source of AC 100 V. The heater load 73 is positioned near the thermocouple 72 and on the right-hand side wall of the vessel 71 at a little lower position like the thermocouple 72. The test concrete members S are arranged and supported by a supporting means (not shown) so that they can be positioned at a little distance from the bottom 71a of the vessel 71. The test concrete members S may by cylinders of a size of 10 cm in diameter and 20 cm long, for example. The test concrete members S after deposition and completion of bleeding are arranged in the vessel 71 together with the formworks used.

In operation, a start button (not shown) of the digital program temperature regulator 70 is pushed, which causes the CPU in the digital program temperature regulator 70 to read out the actually measured data $Df_0$ and time interval information data $Dt_0$ from the data table TBL 1 set up in the RAM incorporated in the program control 81. The firing angle unit control signal Dpc corresponding to the time interval data $Dt_0$ is output from the terminals 81a and 81b of the program control 81. In the firing angle unit 82 the phase control pulse Pp is added to the terminal 83G of the thryistor circuit 83. As the result, the heater load 73 is empowered to heat the test concrete members S. On the other hand, the information on the temperature inside the vessel 71 is fed back to the program control 81 in the digital program temperature regulator 70 by the thermocouple 72, and the temperature inside the vessel 71 is controlled to a temperature corresponding to the actually measured data $Df_0$. This temperature regulation is performed by the operation of the CPU which executes the temperature control program stored in ROM, etc.

When the time interval corresponding to the time interval data $Dt_0$ has elapsed, the CPU reads out the next actually measured data $Df_1$ from address $A_1$, and the temperature inside the vessel 71 is regulated so that it can be kept at a value corresponding to the actually measured data $Df_1$ for the period corresponding to the time interval data $Dt_1$ in the same manner as described above. By so doing, the temperature history inside the vessel 71 becomes the same as the temperature history curve (FIG. 12) data stored in the table TBL 1 set up in the RAM descried above. In other words, the temperature history stored in the table TBL 1 can be established in the vessel 71. Therefore, the test concrete members S arranged in the vessel 71 come to have the same temperature history as that established in the vessel 71.

The test concrete members S can be taken out from the vessel 71 at any desired age and subjected to various tests such as compression test, etc. after capping.

The heat adjustment device shown in FIG. 5 may be replaced by one which comprises a vertical type casing in the form of a hollow cylinder with open upper and lower ends which is adapted to be placed in a liquid tank generally containing water, allowing passage of the liquid therethrough and adjusting the temperature of the liquid in the liquid tank while agitating the liquid, the casing being provided with at least one of a heater for heating the liquid and a cooler for cooling the liquid, a rotary vane for passing the liquid through the casing and agitating it, a driving system for driving the rotary vane and a supporting means for supporting the casing in the liquid or under the liquid surface of the liquid tank.

Figure 13:
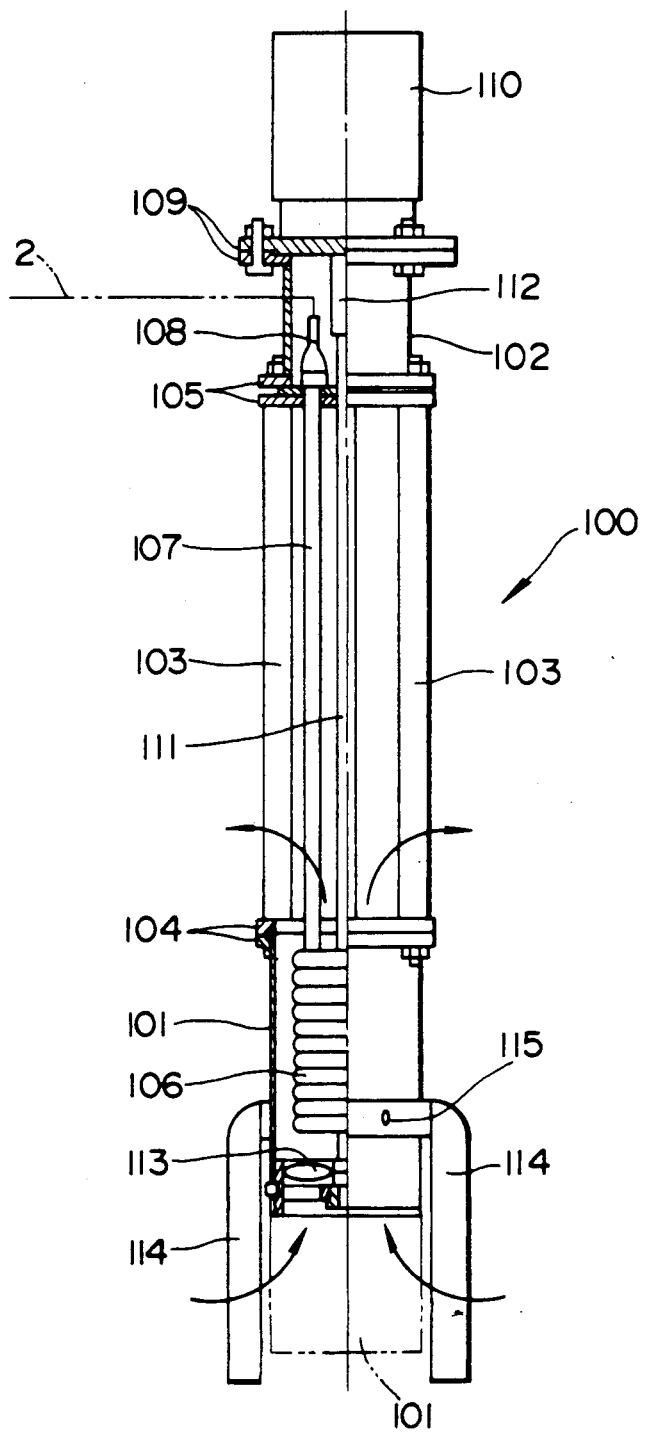
FIG. 13 is a partial sectional view of the heat adjustment device according to one embodiment of this invention.

Referring to FIG. 13 which shows a preferred embodiment of the heat adjustment device which can be used in this invention, reference numeral 100 designates a heat adjustment device having a heater casing 101 and an upper casing 102 which are hollow and cylindrical and connected coaxially with each other through a plurality of connecting rods 103 extending vertically. The heater casing 101 and the upper casing 102 are connected with the connecting rods 103 through respective flanges 104 and 105. The heater casing 101 is a vertical type cylinder which are open at the upper and lower ends thereof and thus allows passage of a liquid such as water therethrough. Inside the casing 101 is provided a helical coil electric heater 106 coaxially with the casing 101. The heater 106 is connected to a cable (not shown) which is guided through an electric source pipe 107. The cable is connected to an electric source cable 150 through a terminal 108 in the upper casing 102 and the output of the heater 106 is regulated by the temperature regulator 119 in FIG. 5.

The upper casing 102 is provided with a flange 109 with which an electric motor (driving mechanism) 110 is attached onto the upper end of the upper casing 102. The driving shaft of the motor 110 is connected with a shaft 111 through a joint 112, the shaft 111 extending downward through the center of the heater 106 and having attached thereto a rotary or agitating vane 113 below the heater 106. The vane 113 is driven by the motor 110 and rotates in a horizontal plane to agitate the water and generate an upward water stream flowing into the inside the heater casing 101.

A foot 114 is provided on the outer surface of the heater casing 101 through a clamp screw 115, which construction makes the heat adjustment device self-supporting. By loosening the clamp screw 115, the foot 114 is allowed to move up and down relatively to the heater casing 101 so that the height of the heat adjustment device 100 from the bottom of the tank 11 (FIG. 5) when the device 100 is self-supporting can be adjusted appropriately. The two-dot chain line in FIG. 13 indicates the lowermost possible position of the heater casing 101. A ring-like connector or girth (not shown) may be provided at the lower end of the foot 114 in order to improve the self-supporting property thereof.

The heat adjustment device 100 described above is used in a self-supporting state such that the heater casing 101 is located at a predetermined height under the water surface of the tank 11 (FIG. 5) and the upper casing 102 and the motor 110 are above the water surface. In operation, the heater 106 is energized and the motor 110 is driven to rotate the vane 113, which causes water in the tank 11 to be sucked in at the lower portion of the heater casing 101, passed through the inside of the heater casing 101 upwardly and flown out of the upper portion thereof, thus agitating the water in the tank, with the water being heated by the heater 106 during the passage through the heater casing 101.

Although the above description relates to heat adjustment with a heater, the heat adjustment device 100 is not limited to employment of the heater. The device 100 may comprise a cooling unit, e.g. a cooling coil for passing cold water or brine, instead of the heater. Alternatively, the device may comprise both a heating unit and a cooling unit as described above so that either one of them can be operated depending on the temperature of the water in the tank. The heater 106 is not limited to electric heaters but those which use thermal media such as hot water, steam, etc. can also be employed. Further, the agitator vane 113 can be positioned above the heater 106 and the direction of water stream may be downward.

The above-described heat adjustment device is advantageous in that uniform temperature distribution is obtained in the tank, a desired temperature of water is obtained precisely, and maintenance of the device is easy.

EXAMPLE 1

Supposing a semi-infinite plate concrete of a minimum size of the member of 1,600 mm, an actualy size test concrete member (actually deposited concrete) C and a model concrete $C_2$ which imitates the actually deposited concrete, both concrete members having the composition as set forth below were prepared and examined using a predicting and controlling apparatus shown in FIGS. 5, 6 and 7 excepting that the casing 31 and the temperature regulator 32 were not used.

Each concrete was a ready mixed concrete whose nominal strength corresponded to 225 kg/cm².

| Formulation | |
|---|---|
| Water-Cement Ratio: | 56.6% |
| Aimed Slump: | 15 cm |
| Aimed Air Ratio: | 4% |
| Fine Aggregate Ratio: Weight | 45.3% |
| Water | 170 kg/cm² |
| C | 300 kg/cm² |
| S | 819 kg/cm² |

-continued

| Formulation | |
|---|---|
| G | 1,012 kg/cm² |

Figure 14:
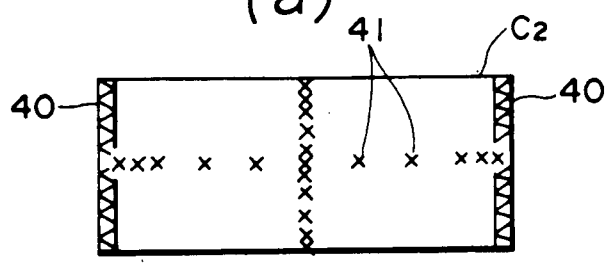
Figure 14:
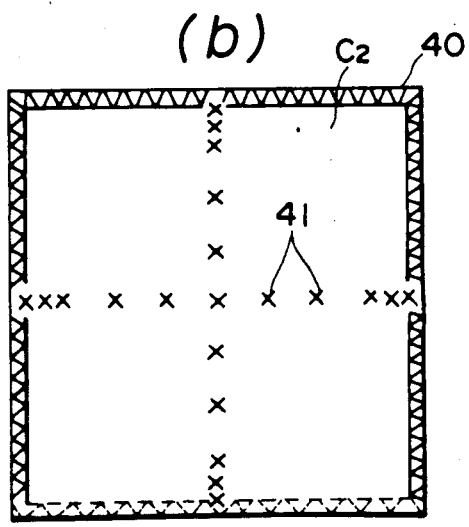
Figure 14:
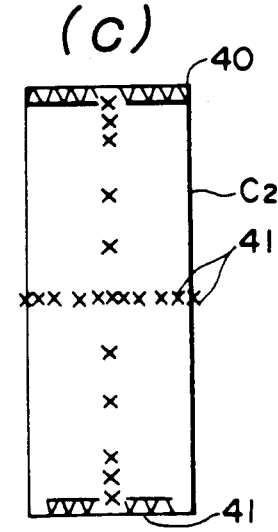

In the above formulation, the following concrete composition was used.
Cement (C): Ordinary Portland Cement
Fine Aggregate (S): Mountain Sand (Maximum Size; 2.5 mm)
Coarse Aggregate (G): Crushed Stone (Maximum Size; 25 mm)
Builder: AE Water Reducing Agent The actual size test concrete members C were formed to have a size of 3,800×3,800×, 1,600 (mm³) and an insulating material 40 was fixed onto each of the boundary surfaces along the width and height of the concrete member as shown in FIG. 14. This was intended to simulate a semi-infinite concrete board having a minimum thickness of 1,600 mm. As the formwork upon deposition of concrete was used, a plywood panel of a thickness of 18 mm was removed at an age of 3 days.

The test concrete member C was measured for its temperature development and change in temperature distribution. The temperature of the concrete was measured using a plurality of thermocouples 17 placed or embedded at reference points 41 shown in FIG. 14.

At the same time, the temperature development and change in temperature distribution of the model concrete $C_2$ were measured at reference points corresponding to those in the actual size test concrete member C.

The results obtained are shown in FIGS. 15 and 16. From these figures, it can be seen that despite the change in the outside air temperature the temperature development and change in temperature distribution of the actual size test concrete member C and those of the model concrete $C_2$ well agreed with each other with high precision. In other words, the predictor obtained from the data of the model concrete $C_2$ accurately grasped the chronological change in the temperature development and temperature distribution. Therefore, with the model concrete $C_2$ the thermal behavior such as heat development, heat conduction and heat transfer of the actual size concrete member C can be simulated exactly, with the result that the chronological change in the temperature development and temperature distribution can be predicted precisely.

FIG. 17 compares the temperature development of the actual size test concrete member C and that of the test concrete member S in the water tank 11. It can be seen from FIG. 17 that the latter adequately corresponds to the former, thus enabling prediction of the strength development of concrete before it is deposited and control of the strength when it is actually deposited.

EXAMPLE 2

Figure 18:
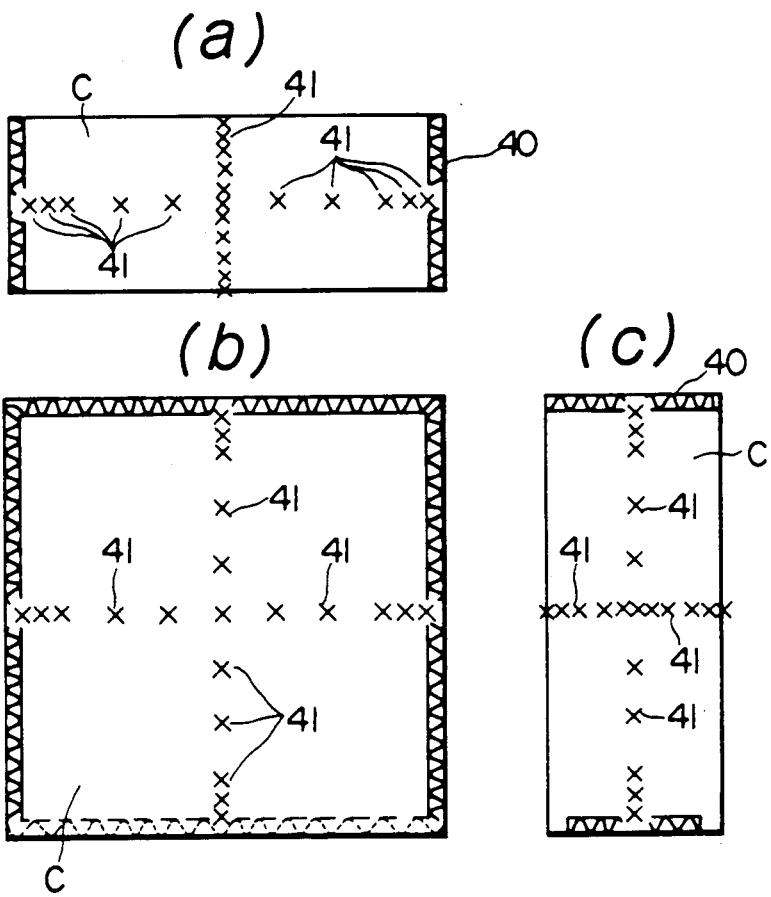

Using the apparatus shown in FIGS. 5, 6 and 7 and the same concrete composition as in Example 1 above, the same procedures as in Example 1 were repeated except that the reference points 41 for the measurement of the temperature of concrete were selected as shown in FIG. 18.

The results obtained are shown in FIG. 19, from which it is apparent that despite the change in the outside air temperature the temperature development and change in temperature distribution of the actual size test concrete member C and those of the model concrete $C_2$ well agreed with each other with high precision.

More particularly, FIG. 19 shows that the central portion of the actual size test concrete member C reached a maximum temperature of 72.8° C. after 45 hours from the deposition while the predictor obtained using the prediction apparatus of this invention was 71.6° C. after 45 hours. In other words, the age of the concrete at which maximum temperature is encountered was agreed between them. Prediction error of temperature was only 1.2° C.

Further, the surface portion of the actual size test concrete member showed a maximum temperature of 50.7° C. 48 hours after the deposition. On the other hand, the predictor was 40.2° C. 51 hours after the deposition. This means that prediction error for predicting the age of concrete when it shows a maximum temperature was 3 hours, and the prediction error for temperature was 0.5° C.

The chronological change in temperature development and temperature distribution were also enough to allow practically acceptable prediction.

EXAMPLE 3

Using the apparatus shown in FIGS. 8 to 11 and the temperature history data of the actually deposited concrete shown in FIG. 12, test concrete member having the same composition as in Example 1 were aged and after capping the aged test concrete members were subjected to compression tests to measure their compression strength and elastic modulus.

The results obtained are shown in FIGS. 20 and 21.

The thermal behavior of concrete in terms of the occurrence of cracks can also be predicted and controlled with high precision by the method and apparatus of this invention. That is, the possibility of the occurrence of cracks in concrete due to stress therein can be evaluated based on the temperature distribution coefficient of concrete obtained from the temperature development of the concrete.

FIG. 22 shows a system for the prediction of the occurrence of cracks according to an embodiment of this invention. The crack prediction system comprises a temperature prediction device 201, a thermal conduction analyzer 201a, a data processing device 202 such as a personal computer connected to the temperature prediction device 201 and the thermal conduction analyzer 201a, a printer 203 and a plotter 204 both connected to the data processing device 202 and a display device 205 connected to the printer 3. The temperature prediction device 201 measures the temperature development of a mass concrete using a simulation device, such as the device as shown in FIGS. 5 to 7. The temperature data measured are input into the data processing device 202 as a temperature predictor. The thermal conduction analyzer 201a comprises a microcomputer which calculates the temperature development value of the mass concrete from the heat conductivity, heat diffusivity, specific heat, heat transfer coefficient, etc. and records the calculated values in the data processing device 202 independently of the temperature prediction device 201.

The data processing device 202 is adapted to automatically calculate a temperature distribution coefficient $F_0$ or $F_{00}$ from the temperature predictors or calculated values of the temperature development, compare $F_{00}$ values thus-obtained with data shown in FIG. 24 below, and judge if there is a possibility of the occurrence of cracks and outputs the results. The printer 203 and the plotter 204 prepare a drawing or graph respresenting the results obtained by the operation of the data processing device 202. The display device 205 comprises an automatic display board which can issue a warning by lighting a lamp or sounding a buzzer or bell.

The data processing device 202 is connected to a measurement device 207 for measuring the temperature develoment of an actually deposited concrete 206, and the temperature development data are input in the data processing device 202.

The possibility of the occurrence of cracks is evaluated by (1) predicting the temperature development of a mass concrete using the temperature prediction device 201, (2) evaluating outer constraint conditions, (3) calculating temperature distribution coefficient $F_0$ or $F_{00}$ using the data processing device 202, and (4) evaluating by the data processing device 202 the possibility of the occurrence of cracks based on the temperature distribution coefficient obtained. The temperature distribution coefficient $F_{00}$ is recorded by the printer 203 and the plotter 204. When the data processing device 202 evaluates that the possibility of the occurrence of cracks is greater than a predetermined significance level by the value of $F_0$ or $F_{00}$, the display device 205 issues a warning by lighting a lamp or sounding a buzzer. In the system of this invention, what must be actually measured are only temperature development data. Experiments and measurement of various physical properties and analysis of thermal stress and further experiments and search on the strength of concrete which have been heretofore been necessary in conventional methods are unnecessary, with the result that evaluation of the possibility of the occurrence of cracks in a mass concrete can be performed with ease.

When a mass concrete is actually constructed the temperature development of the concrete member can be measured and the temperature distribution coefficient $F_0$ or $F_{00}$ thereof is calculated using the data processing device 202 followed by comparing the calculated data with previously obtained predictors to see if there is a significant difference therebetween and issuing a warning if necessary, thus enabling control or management of the occurrence of cracks in a mass concrete.

There are two kinds of temperature distribution coefficient $F_0$ and $F_{00}$. $F_0$ is calculated when the rate of temperature change of concrete is high and $F_{00}$ is obtained for a low rate of temperature change of concrete.

1. $F_0$

A formula for the calculation of an elastic temperature stress is generally composed of two portions, one being a function of a linear expansion coefficient $\alpha(°C.^{-1})$, a Poisson ratio $v$ and elastic modulus $E(kg/cm^2)$ and another being a function of temperature $T$ (°C.) and distance $r$ from the center (cm).

Expressing the portion of the formula with variables $T$ and $r$ as $F(T, r)$ elastic temperature stress $\sigma_\theta$ is generally given as follows.

$$\sigma_\theta = \alpha E \frac{1}{1-v} F(T,r) \quad (1)$$

When a mass concrete is a solid disc, $F(T, r)$ in the circumferential direction of the disc is given by equation (2) below.

$$F(T,r) = \frac{1}{r^2} \int_0^r T(r)rdr + \frac{1}{r_0^2} \int_0^{r_0} T(r)rdr - T(t) \quad (2)$$

wherein $r_0$ is a radius (cm) of the disc and $T(r)$ is the temperature of the position r.

Supposing cracks occur when a maximum tensile stress $\sigma_{\theta max}$ coincides with a tensile strength ft, and assuming $_{max}$ occurs at the position rm, equation (4) below is obtained from the equation (1) above.

$$\frac{\sigma_{\theta max}}{ft} = \frac{\alpha}{1-v} \cdot \frac{E}{ft} \cdot F(T,r=rm) = 1 \quad (4)$$

Further, supposing an elastic strain is approximately expressed by $\epsilon = \sigma/E$, and assuming cracks occur when a maximum tensile strain coincides with a constant strain ability $\epsilon_0$, equation (5) below is given.

$$\frac{\sigma_{\theta max}}{\epsilon_0} = \frac{\alpha}{1-v} \cdot \frac{1}{\epsilon_0} \cdot F(T,r=rm) = 1 \quad (5)$$

wherein rm is a distance of the position where the maximum tensile stress (or strain) appears from the center (cm).

Here, let us assume the relationship $\alpha/(1-v)=$ constant approximately is valid. Then, the conditions of the occurrence of cracks are expressed as $F(T, rm) \times E/ft = a$ (constant). From this, it follows that if there is a definite or proportional relationship between E and ft there will logically be a definite relationship between F(T, rm) and the conditions of crack formation. From the equation (5) above F(T, rm)=b (constant) stands for the conditions of crack formation and thus it is possible to evaluate the possibility of crack formation by the value or magnitute of F(T, rm).

With the above consideration, it is now found that the value of F(T, rm) which is a function of the temperature (T) and distance (rm) at the position r=rm where a maximum tensile temperature stress and a maximum tensile strain appear can be defined as a temperature distribution coefficient $F_0$ and the relationship between the value of $F_0$ and temperature crack formation can be considered.

The temperature distribution coefficient $F_0$ in the circumferential direction of a solid disc is now given by equation (6) below.

$$\begin{aligned} F_0(disc) &= F(T,r=rm) \\ &= \frac{1}{rm^2} \int_0^{rm} T(r)rdr + \\ &\quad \frac{1}{r_0^2} \int_0^{r_0} T(r)rdr - T(rm) \end{aligned} \quad (6)$$

As for a mass concrete having a rectangular cross-section, the position r is located at a distance h from the central axis of the cross-sectional area F(T, h) is expressed by equation (7) and the temperature distribution coefficient $F_0$ is given by equation (8) below.

$$F(T,h) = \frac{1}{2h_0} \int_{h_0}^{h_0} T(h)dh + \frac{3h}{2h_0^3} \int_{-h_0}^{h_0} T(h)hdh - T(h) \quad (7)$$

$$F_0 \text{ (rectangular plate)} = F(T, h = h_m) = \frac{1}{2h_0} \int_{-h_0}^{h_0} T(h)dh + \quad (8)$$

$$\frac{3h_m}{2h_0^3} \int_{-h_0}^{h_0} T(h)h\,dh - T(h_m)$$

wherein h is a distance from the center of the rectangular cross-sectional area (cm), $h_0$ is a distance between the central axis and the surface, and $h_m$ is a distance of the position where a maximum tensile temperature stress (or strain) appears from the central axis (cm).

Since $\sigma_{\theta max}$ or $\epsilon_{\theta max}$ appear on the outer peripheral surface of the disc, the condition of $r_m = r_0$ can be introduced into the equation (6) to obtain the temperature distribution coefficient of a disc-form mass concrete as expressed in equation (9) below.

$$F_0 = \frac{2}{r_0^2} \cdot \int_0^{r_0} T(r)r\,dr - T(r_0) \quad (9)$$

In the equation (9)T(r), a temperature distribution state of a mass concrete in the radial direction, can be approximated by actually measured value, which is then introduced in the equation (9), thus enabling calculation of the value of $F_0$.

FIG. 23 is a graph showing the relationship among the results of crack tests, $F_0$ values and the tensile strength reduction ratio using a plurality of mass concrete test members (thickness: 100 mm; diameter: 200 mm, 350 mm or 700 mm). The mass concrete test members are provided with a heater in the center of each of upper and lower surfaces thereof, and the upper and lower surfaces are covered with an insulating material. Inside the test concrete members are embedded a plurality of temperature sensors in order to actually measure the temperature of the concrete at various reference points. The concrete is heated with the heater to forcibly generate temperature differences between the surface portion and central portion thereof. The temperature difference is set in a range of between 10° C. and 50° C. for one group, and another group is allowed to undergo temperature elevation as is. The rate of increase in temperature difference is about 30° C./h.

In the above crack tests, those test concrete members which show no crack formation are subjected to tensile strength tests in order to obtain tensile strength f't kg/cm² according to the method of JIS 1113 with maintaining the temperature difference between the central portion and the outer surface portion of the test member at a constant level with a view to indirectly evaluate the magnitude of temperature strain generated. On the other hand, test concrete members which have the same shape and size as the above test concrete members, but have not been heated, are subjected to tests for tensile strength ft (kg/cm²). The tensile strength reduction ratio (%) is obtained from f't and ft above according to equation (10) below.

$$\text{Tensile Strength Reduction Ratio(\%)} = \frac{ft - f't}{ft} \times 100 \quad (10)$$

FIG. 23 shows the relationship between the tensile strength reduction ratio and the temperature distribution coefficient $F_0$ of each test concrete member calculated based on the equation (10).

From the results shown in FIG. 23, it is apparent that the state of the occurrence of cracks when the rate of temperature change of a mass concrete is high can be grasped using temperature distribution coefficient $F_0$ as an index. It is also apparent that the state of a mass concrete can be classified into four groups depending on the value of $F_0$.
1) Safety zone (0° C. $\leq F_0 \leq$ 6° C.)
2) Danger zone (6° C. $< F_0 \leq$ 9° C.)
3) Crack formation limit (9° C. $< F_0 \leq$ 12° C.)
4) Crack formation zone ($F_0 >$ 12°)
2. $F_{\infty}$ When the rate of temperature change is low and stress or strain grows gradually, the temperature stress of a mass concrete is greatly affected by the progress of flow of concrete. Therefore, the temperature distribution coefficient under unnegligible influence by the flow of concrete $F_0$ need be corrected using a correction factor R described hereinbelow.

When the influence of the flow of concrete is disregarded, the relationship between $F_0$ and maximum tensile temperature stress $\sigma_{\theta max}$ is given by equation (11) below regardless of the shape and direction thereof. Further, supposing elastic strain $\epsilon$ is approximately expressed as $\epsilon = \sigma/E$ the relationship between $F_0$ and maximum tensile strain $\epsilon_{\theta max}$ is expressed by equation (12) below.

$$\sigma_{\theta max} = \frac{\alpha}{1 - \nu} EF_0 \quad (11)$$

$$\epsilon_{\theta max} = \frac{\alpha}{1 - \nu} F_0 \quad (12)$$

Taking the influence of the flow of concrete into consideration and assuming true elastic modulus after time t counting from the initiation of temperature change at the age of the material being $t_0$ is $E'(t, t_0)$, the actually occurring temperature stress $\sigma_{max}$ is given by equation (13).

$$\sigma'_{\theta max} = \frac{\alpha}{1 - \nu} E(t, t_0) \times F_0 \quad (13)$$

Here, the amount or degree of the influence of the flow of concrete at time t > 1 (hour) will be evaluated, taking into consideration the fact that when the rate of temperature change is high, t is about 1 to 2 hours and the fact that with ordinary concrete construction there is no possibility where cracks occur within 1 hour unless there occurs an accident, and thus selecting t = 1 (hour) as a standard.

That is, $E'(t, t_0)$ at a desired time is given by equation (14) below by adopting $E'(t, t_0)$ at t = 1 (hour) as a standard and $R(t, t_0)$ is obtained by experiments, thus enabling the evaluation of the amount of the flow of concrete. Substitution of equation (14) below in the equation (13) gives rise to equation (15) below.

$$E'(t, t_0) = \frac{E'(t = 1, t_0)}{1 + R(t, t_0)} \quad (14)$$

$$\sigma_{\theta max} = \frac{\alpha}{1 - \nu} \cdot \frac{E'(t, t_0)}{1 + R(t, t_0)} \times F_0 \quad (15)$$

Further, assuming that in the thermal behavior in the case where the influence of the flow of concrete cannot be neglected, temperature crack formation will occur when maximum tensile temperature stress $\sigma'_{\theta max}$ after correction with respect to the influence of the flow of concrete coincides with the tensile strength ft of concrete, upon the occurrence of cracks equation (16) below can be derived from equation (15).

$$\frac{\alpha}{1-\nu} \cdot \frac{E'(t=1, t_0)}{ft} \times \frac{F_0}{1+R(t,t_0)} = \frac{\sigma'_{max}}{ft} = 1 \quad (16)$$

Assuming cracks occur when $\sigma_{\theta max}$ coincides with the tensile strength of concrete in the equations (11) and (12) above applicable to the cases where relatively steep temperature change is involved, equation (17) can be derived from equation (11), or assuming cracks occur when $\epsilon_{\theta max}$ coincides with strain ability $\epsilon_\theta$ of concrete, upon crack formation equation (18) below can be obtained from equation (12).

$$\frac{\sigma_{\theta max}}{ft} = \frac{\alpha}{1-\nu} \cdot \frac{E}{ft} \times F_0 = 1 \quad (17)$$

$$\frac{\epsilon_{\theta max}}{\epsilon_0} = \frac{\alpha}{1-\nu} \cdot \frac{1}{\epsilon_0} F_0 = 1 \quad (18)$$

Substitution of the condition that $F_0$ approximately is a constant in equations (17) and (18), the following equations (19) and (20) are derived.

$$\frac{\alpha}{1-\nu} \cdot \frac{E}{ft} = \frac{1}{F_0} \approx A(\text{constant})$$

$$\frac{\alpha}{1-\nu} \cdot \frac{1}{\epsilon_0} = \frac{1}{F_0} \approx B(\text{constant})$$

Since equation (19) is derived so as to be applicable to the case where relatively steep change in temperature occurs, the following equation (21) for $E'(t=1$ hour, $t_0)$ at a standard time of $t=1$ hour which is selected taking the influence of the flow of concrete into consideration is obtained. In addition, substitution of equation (21) in equation (16) results in equation (22) below, which shows the relationship between the maximum tensile temperature stress $\sigma'_{\theta max}$ after correction with respect to the influence of the flow of concrete and temperature distribution coefficient $F_0$.

$$\frac{\alpha}{1-\nu} \cdot \frac{E'(t=1, t_0)}{ft} \approx A(\text{constant})$$

$$\frac{\sigma'_{\theta max}}{ft} \approx A(\text{constant}) \times \frac{F_0}{1+R(t,t_0)} \quad (22)$$

From equation (22), it can be judged that evaluation of the possibility of the occurrence of temperature cracks based on the relationship between the maximum tensile temperature stress after correction with respect to the influence of the flow of concrete and the tensile strength of concrete is approximately equivalent to evaluation based on the amount or degree expressed by $F_0/(1+R)$ with introduction of the correction factor R.

Defining the temperature distribution coefficient after correction with a correction factor R as $F_{00}$, equation (23) below is obtained.

$$F_{00} = \frac{F_0}{1+R(t,t_0)} \quad (23)$$

wherein time after the initiation of temperature change t is longer than 1 hour ($t>1$).

EXAMPLE OF CALCULATION OF $F_{00}$

A rectangular test concrete member having a size of 400 mm in width, 1,200 mm in length and 125 mm in thickness was prepared and a heater was positioned at the center of the surface of member. The whole concrete member and the heater were covered with an insulating material to form a test model. $F_{00}$ value of the rectangular concrete board when it was forcibly heated with the heater was calculated as follows.

In this test, the maximum tensile temperature stress appeared in the direction of the length or the longest edge of the rectangular concrete board and the temperature distribution coefficient $F_0$ was given by equation (24) based on equation (8) above.

$$F_0 = \frac{1}{2C} \int_{-c}^{c} T(y)dy + \frac{3y}{2C^3} \int_{-c}^{c} T(y)ydy - T(y=\pm C) \quad (24)$$

wherein C is a distance between the central axis and the surface of the rectangular concrete board (=half the thickness of the board).

The temperature distribution in the direction of the shortest edge of the rectangular concrete is symmetrical with respect to the central axis thereof and therefore the second term in equation (24) is cancelled to give equation (25) below.

$$F_0 = \frac{1}{2C} \int_{-c}^{c} T(y)dy - T(y=\pm C) \quad (25)$$

That is, $F_{00}$, temperature distribution coefficient of the rectangular concrete board after correction with respect to the influence of the flow of concrete can be calculated by correcting the $F_0$ value calculated according to equation (25) based on equation (23) above.

Various formulae for calculating $R(t, t_0)$ were obtained by experiments, and it was confirmed that the R value for the time range up to 12 hours from the deposition of a concrete when the concrete is still very flowable can be calculated by the equation $R=1.63 \log t + 0.696 (\log t)^2$.

For example, the R value for the above-described test concrete member at its age of 12 hours, i.e. R(12 hr., 0 hr.) was calculated by introducing the condition $t=12$ into the above equation to obtain $R=2.57$. Further, $F_0$ value for the test concrete member was calculated according to the equation (25) to obtain $F_0=17.55$.

Now, introducing $F_0=17.55$ and $R(t, t_0)=17.55$ into the equation (23) above, $F_{00}=4.92$ was obtained.

In order to obtain chronological change in $F_{00}$, suitable $R(t, t_0)$ values were calculated from equations (26), (27) and (28) below.

$$R(t, t_0) = a\log t + b(\log t)^2 \quad (26)$$

$$a = (1.345 - 0.572 \log t_0)^{\frac{1}{2}} \quad (27)$$

$$b = 0.1856 - 0.0834 \log t_0 \quad (28)$$

FIG. 24 shows the relationship between the tensile strength reduction ratio and the temperature distribution coefficient $F_{00}$ of various test concrete members calculated based on the above-described equations.

From the results shown in FIG. 24, it is apparent that the state of the occurrence of cracks when the rate of temperature change of a mass concrete is low can be grasped using temperature distribution coefficient $F_{00}$ as an index. It is also apparent that the state of a mass concrete can be classified into four groups depending on the value of $F_{00}$.

1) Safety zone ($0°\text{ C.} \leq F_{00} \leq 6°\text{ C.}$)
2) Danger zone ($6°\text{ C.} < F_{00} \leq 9°\text{ C.}$)
3) Crack formation limit ($9°\text{ C.} < F_{00} \leq 12°\text{ C.}$)
4) Crack formation zone ($F_{00} > 12°\text{ C.}$)

Therefore, prediction and control of the occurrence of cracks in a mass concrete can be performed easily and precisely by inputting the above-described equations in the data processing device 202, operating the data processing device 202 to process the data measured by the temperature prediction device 201 and calculate $F_{00}$ based thereon, applying the resultant value to the criterion 1) to 4) above, and issue a warning on the display device 205 by the instruction from the data processing device 202 when the results indicate that there is a danger or high possibility of the occurrence of cracks.

FIG. 25 shows temperature crack formation in concrete under various experimental conditions. From the results shown in FIG. 25, it can be seen that when $F_{00}$ is in the safety zone no concrete member forms cracks while cracks occur in all of the concrete members that show $F_{00}$ values in the crack formation zone. It is believed that according as $F_{00}$ values increase after entering the danger zone up to the crack formation limit zone the concrete members will form cracks one after another. Therefore, evaluation of the possibility of the occurrence of cracks using $F_{00}$ as an index can be applied to actually deposited concrete.

What is claimed is:

1. A method for predicting and controlling strength development of concrete, comprising:
    (1) placing a test concrete member having a composition in a vessel which is regulated with respect to temperature thereof,
    (2) measuring the temperature inside the vessel,
    (3) recording temperature data in a data memory means and a data processing means,
    (4) transmitting data on temperature of a reference concrete having a composition which is the same as said test concrete member selectively from said reference concrete in real time and from said data memory means and said data processing means which store data on the temperature of a reference concrete previously obtained via a data transmission means to a temperature regulator for regulating temperature inside said vessel,
    (5) regulating the temperature of said vessel based on said data selectively from said reference concrete and from said memory means and on said data on the temperature inside said vessel from said memory means so that a temperature history of said test concrete member can simulate a temperature history of said reference concrete,
    (6) measuring strength of said test concrete member at its different ages, collecting data on the strength of said test concrete member, and
    (7) processing said strength data in said data processing means.

2. The method as claimed in claim 1, wherein said reference concrete is an actually deposited concrete.

3. The method as claimed in claim 2, further comprising separately collecting data on the temperature history of a model concrete, comparing said temperature history data with said data on the temperature history of said actually deposited concrete, and issuing a warning signal when a difference between the data of said model concrete and the data of said actually deposited concrete exceeds a predetermined level.

4. The method as claimed in claim 1, wherein said reference concrete is a model concrete.

5. The method as claimed in claim 1, further comprising displaying said data on the temperature history of said reference concrete and said data on the temperature inside said vessel.

6. The method as claimed in claim 1, wherein said vessel is an insulated tank having a quadrilateral transverse cross-section and having four insulating peripheral walls, both ends of said insulated tank being covered with a casing to form a cavity for controlling the temperature and wherein said test concrete member is placed in said cavity.

7. The method as claimed in claim 6, wherein said data on the strength of said test concrete member is expressed in terms of occurrence of cracks.

8. The method as claimed in claim 1, wherein said transmission means is one selected from a group consisting of an optical fiber transmission line, a wireless telecommunication means, a telephone system, and a light transmission system.

9. The method as claimed in claim 1, wherein said regulation is performed by means of a digital program temperature regulator.

10. The method as claimed in claim 1, wherein said measurement of the temperature of said vessel is performed by means of a plurality of thermocouples.

11. A method for predicting and controlling strength development of concrete, comprising:
    (1) placing a test concrete member having a composition in a vessel which is regulated with respect to temperature thereof,
    (2) measuring the temperature inside the vessel,
    (3) recording temperature data in a data memory means and a data processing means,
    (4) transmitting data on temperature of a reference concrete having a composition which is the same as said test concrete member selectively from said reference concrete in real time and from said data memory means and said data processing means which store data on the temperature of a reference concrete previously obtained via a data transmission means to a temperature regulator for regulating temperature inside said vessel,
    (5) regulating the temperature of said vessel based on said data selectively from said reference concrete and from said memory means and on said data on the temperature inside said vessel from said memory means so that a temperature history of said test concrete member can simulate a temperature history of said reference concrete,
    (6) measuring strength of said test concrete member at its different ages, collecting data on the strength of said test concrete member, and
    (7) processing said strength data in said data processing means, wherein said vessel is a water tank containing water in which said test concrete member is submerged.

12. The method as claimed in claim 11, wherein said regulation of the temperature inside said water tank is performed using a heat adjustment device.

13. An apparatus for predicting and controlling strength development of concrete, comprising:
- (1) a vessel for receiving therein a test concrete member having a composition,
- (2) a temperature regulating means,
- (3) a temperature controlling unit operatively connected to said temperature regulating means for controlling temperature inside said vessel,
- (4) a data recording means for selectively recording a chronological change of the temperature of a reference concrete said reference concrete having the same composition as said test concrete member and being located at a distance from said test concrete member,
- (5) a data transmitting means for transmitting data selectively to said data recording means from one of said reference concrete and a temperature measuring means in order to use the temperature of said reference concrete as a model, and
- (6) a computer operatively connected to said data recording means for processing the data from said data recording means.

* * * * *